(12) United States Patent
Blondelle et al.

(10) Patent No.: US 7,960,339 B2
(45) Date of Patent: Jun. 14, 2011

(54) ANTIMICROBIAL PEPTIDES

(75) Inventors: Sylvie E. Blondelle, San Diego, CA (US); Roman Jerala, Ljubljana (SI); Primoz Pristovsek, Ajdovscina (SI); Andreja Majerle, Ljubljana (SI); Mateja Zorko, Podbocje (SI); Bostjan Japelj, Vrhnika (SI); Klaus Brandenburg, Hamburg (DE); Jorg Andra, Hamburg (DE); Massimo Porro, Siena (IT); Ignacio Moriyon Uria, Pamplona (ES); Jose Leiva Leon, Cizur (ES); Guillermo Martinez de Tejada de Garaizabal, Pamplona (ES); Dagmar Zweytick, Graz (AT); Gunter Deutsch, Edelsbach (AT); Karl Lohner, Graz (AT)

(73) Assignee: Österreichische Akademie der Wissenschaften, Graz (AT)

( * ) Notice: Subject to any disclaimer, the term of this patent is extended or adjusted under 35 U.S.C. 154(b) by 329 days.

(21) Appl. No.: 12/373,272

(22) PCT Filed: Jul. 10, 2007

(86) PCT No.: PCT/AT2007/000345
§ 371 (c)(1),
(2), (4) Date: Jan. 9, 2009

(87) PCT Pub. No.: WO2008/006125
PCT Pub. Date: Jan. 17, 2008

(65) Prior Publication Data
US 2009/0233870 A1   Sep. 17, 2009

(30) Foreign Application Priority Data

Jul. 10, 2006 (AT) .................. A 1165/2006

(51) Int. Cl.
*A61K 38/00* (2006.01)
(52) U.S. Cl. ............................................. 514/2.3
(58) Field of Classification Search .................. None
See application file for complete search history.

(56) References Cited

U.S. PATENT DOCUMENTS

| 6,476,189 B1 | 11/2002 | Yamakawa | 530/328 |
| 6,890,902 B2 | 5/2005 | Svendsen et al. | 514/12 |
| 2004/0072990 A1 | 4/2004 | Tzeng et al. | 514/12 |

FOREIGN PATENT DOCUMENTS

| WO | WO 01/23417 | 4/2001 |
| WO | WO 01/34641 | 5/2001 |
| WO | WO 2005/033267 | 4/2005 |
| WO | WO 2005/118626 | 12/2005 |
| WO | WO 2006/050611 | 5/2006 |

OTHER PUBLICATIONS

Andra et al., "Enhancement of endotoxin neutralization by coupling of a C12-alkyl chain to a lactoferricin-derived peptide," *Biochem. J.*, 385 (pt. 1): 135-143, 2005.
Austrian Search Report, issued in Int. App. No. 4B R 354/2006, mail date Jul. 28, 2006.
Bickel et al., "Delivery of peptides and proteins through the blood-brain barrier," *Adv. Drug Deliv. Rev.*, 46: 247-279, 2001.
Chen et al., "Antibacterial activity of short hydrophobic and basic-rich peptides," *Am. J. Vet. Res.*, 64 (9): 1088-1092, 2003.
Farnaud et al., "Variation in antimicrobial activity of lactoferricin-derived peptides explained by structure modelling," *FEMS Microbiol. Lett.*, 238 (1): 221-226, 2004.
International Search Report and Written Opinion, issued in Int. App. No. PCT/AT2007/000345, mail date Nov. 27, 2007.
Japelj et al., "Structural origin of endotoxin neutralization and antimicrobial activity of a lactoferrin-based peptide," *J. of Biological Chemistry*, 280 (17): 16955-16961, 2005.
Kompella et al., "Delivery systems for penetration enhancement of peptide and protein drugs: design considerations," *Adv. Drug Deliv. Rev.*, 46 (1-3): 211-245, 2001.
Staubitz et al., "Structure-function relationships in the tryptophan-rich, antimicrobial peptide indolicidin," *J. of Peptide Science*, 7 (10): 552-564, 2001.
Strøm et al., "Increased antibacterial activity of 15-residue murine lactoferricin derivatives," *J. Peptide Res.*, 57 (2): 127-139, 2001.
Takahashi et al., "Multidisciplinary treatment by pneumonectomy, PMX and CHDF in a case of pulmonary suppuration complicated with septic shock," *Ann. Thorac. Cardiovasc. Surg.*, 9 (5): 319-322, 2003.

*Primary Examiner* — Christina Bradley
(74) *Attorney, Agent, or Firm* — Fulbright & Jaworski L.L.P.

(57) ABSTRACT

The present invention relates to families of polypeptides and lipopolypeptides that have antimicrobial and endotoxin-neutralizing activities. These molecules show a broad spectrum of activity against various pathogens (including bacteria, viruses, fungi etc.) These compounds can be used alone or in combination therapy with conventional antibiotics or antiendotoxic agents. In addition, the present invention discloses processes for making and using of the compounds.

34 Claims, 4 Drawing Sheets

SEQUENCE LISTING

<160> NUMBER OF SEQ ID NOS: 87

<210> SEQ ID NO 1
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 1

Phe Trp Gln Arg Ile Arg Lys Val Arg
1               5

<210> SEQ ID NO 2
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 2

Phe Trp Gln Arg Arg Ile Arg Lys Val Arg Arg
1               5                   10

<210> SEQ ID NO 3
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 3

Phe Trp Gln Arg Lys Ile Arg Lys Val Arg Lys
1               5                   10

<210> SEQ ID NO 4
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 4

Phe Trp Gln Arg Asn Ile Arg Ile Arg Arg
1               5                   10

<210> SEQ ID NO 5
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 5

Phe Trp Gln Arg Asn Ile Arg Lys Val Arg
1               5                   10

<210> SEQ ID NO 6
<211> LENGTH: 9
<212> TYPE: PRT
<213> ORGANISM: Artificial
<220> FEATURE:

-continued

<223> OTHER INFORMATION: Peptide exhibiting antimicrobial and/or
      endotoxin-neutralizing activity

<400> SEQUENCE: 6

Phe Trp Gln Arg Asn Ile Arg Val Arg
1               5

<210> SEQ ID NO 7
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 7

Phe Trp Gln Arg Asn Ile Arg Lys Val Arg Arg
1               5                   10

<210> SEQ ID NO 8
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 8

Phe Trp Gln Arg Asn Ile Arg Lys Val Lys Lys
1               5                   10

<210> SEQ ID NO 9
<211> LENGTH: 12
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 9

Phe Trp Gln Arg Asn Ile Arg Lys Val Arg Arg Arg
1               5                   10

<210> SEQ ID NO 10
<211> LENGTH: 12
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 10

Phe Trp Gln Arg Asn Ile Arg Lys Val Lys Lys Lys
1               5                   10

<210> SEQ ID NO 11
<211> LENGTH: 13
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 11

Phe Trp Gln Arg Asn Ile Arg Lys Val Arg Arg Arg Arg
1               5                   10

<210> SEQ ID NO 12

```
<211> LENGTH: 13
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 12

Phe Trp Gln Arg Asn Ile Arg Lys Val Arg Arg Arg Ile
1               5                   10

<210> SEQ ID NO 13
<211> LENGTH: 13
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 13

Phe Trp Gln Arg Asn Ile Arg Lys Val Lys Lys Lys Lys
1               5                   10

<210> SEQ ID NO 14
<211> LENGTH: 13
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 14

Phe Trp Gln Arg Asn Ile Arg Lys Val Lys Lys Lys Ile
1               5                   10

<210> SEQ ID NO 15
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 15

Phe Trp Gln Arg Asn Ile Arg Lys Ile Arg
1               5                   10

<210> SEQ ID NO 16
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 16

Phe Trp Gln Arg Asn Ile Arg Lys Leu Arg
1               5                   10

<210> SEQ ID NO 17
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 17

Phe Trp Gln Arg Asn Ile Arg Lys Trp Arg
```

```
                    1               5                  10

<210> SEQ ID NO 18
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 18

Phe Trp Gln Arg Asn Trp Arg Lys Val Arg
1               5                  10

<210> SEQ ID NO 19
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 19

Phe Trp Gln Arg Asn Phe Arg Lys Val Arg
1               5                  10

<210> SEQ ID NO 20
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 20

Phe Trp Gln Arg Asn Tyr Arg Lys Val Arg
1               5                  10

<210> SEQ ID NO 21
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 21

Phe Trp Gln Arg Asn Ile Arg Lys Val Ser
1               5                  10

<210> SEQ ID NO 22
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 22

Phe Trp Gln Arg Arg Ile Arg Ile Arg Arg
1               5                  10

<210> SEQ ID NO 23
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity
```

```
<400> SEQUENCE: 23

Phe Trp Gln Arg Pro Ile Arg Lys Val Arg
1               5                   10

<210> SEQ ID NO 24
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 24

Phe Trp Gln Arg Arg Ile Arg Lys Trp Arg
1               5                   10

<210> SEQ ID NO 25
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 25

Phe Trp Gln Arg Arg Ile Arg Arg Trp Arg Arg
1               5                   10

<210> SEQ ID NO 26
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 26

Phe Trp Pro Arg Asn Ile Arg Lys Val Arg
1               5                   10

<210> SEQ ID NO 27
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 27

Phe Trp Ala Arg Asn Ile Arg Lys Val Arg
1               5                   10

<210> SEQ ID NO 28
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 28

Phe Trp Ile Arg Asn Ile Arg Lys Val Arg
1               5                   10

<210> SEQ ID NO 29
<211> LENGTH: 10
<212> TYPE: PRT
```

-continued

```
<213> ORGANISM: Artificial
<220> FEATURE:
<223> OTHER INFORMATION: Peptide exhibiting antimicrobial and/or
      endotoxin-neutralizing activity

<400> SEQUENCE: 29

Phe Trp Leu Arg Asn Ile Arg Lys Val Arg
1               5                   10

<210> SEQ ID NO 30
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 30

Phe Trp Val Arg Asn Ile Arg Lys Val Arg
1               5                   10

<210> SEQ ID NO 31
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 31

Phe Trp Gln Arg Asn Ile Phe Lys Val Arg
1               5                   10

<210> SEQ ID NO 32
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 32

Phe Trp Gln Arg Asn Ile Tyr Lys Val Arg
1               5                   10

<210> SEQ ID NO 33
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 33

Phe Ala Trp Gln Arg Asn Ile Arg Lys Val Arg
1               5                   10

<210> SEQ ID NO 34
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 34

Phe Ile Trp Gln Arg Asn Ile Arg Lys Val Arg
1               5                   10
```

```
<210> SEQ ID NO 35
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 35

Phe Leu Trp Gln Arg Asn Ile Arg Lys Val Arg
1               5                   10

<210> SEQ ID NO 36
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 36

Phe Val Trp Gln Arg Asn Ile Arg Lys Val Arg
1               5                   10

<210> SEQ ID NO 37
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 37

Phe Trp Arg Ile Arg Lys Trp Arg
1               5

<210> SEQ ID NO 38
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 38

Phe Trp Arg Ile Arg Lys Val Arg
1               5

<210> SEQ ID NO 39
<211> LENGTH: 6
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 39

Phe Trp Arg Trp Arg Arg
1               5

<210> SEQ ID NO 40
<211> LENGTH: 7
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 40
```

```
Phe Trp Arg Arg Trp Arg Arg
1               5

<210> SEQ ID NO 41
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 41

Phe Trp Arg Arg Trp Ile Arg Arg
1               5

<210> SEQ ID NO 42
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 42

Phe Trp Arg Gly Trp Arg Ile Arg Arg
1               5

<210> SEQ ID NO 43
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 43

Phe Trp Arg Arg Phe Trp Arg Arg
1               5

<210> SEQ ID NO 44
<211> LENGTH: 7
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 44

Phe Trp Arg Trp Arg Trp Arg
1               5

<210> SEQ ID NO 45
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 45

Phe Trp Arg Ile Trp Arg Trp Arg
1               5

<210> SEQ ID NO 46
<211> LENGTH: 9
<212> TYPE: PRT
<213> ORGANISM: Artificial
<220> FEATURE:
```

<223> OTHER INFORMATION: Peptide exhibiting antimicrobial and/or
      endotoxin-neutralizing activity

<400> SEQUENCE: 46

Phe Trp Arg Ile Trp Arg Ile Trp Arg
1               5

<210> SEQ ID NO 47
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 47

Phe Trp Arg Asn Ile Arg Lys Trp Arg
1               5

<210> SEQ ID NO 48
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 48

Phe Trp Arg Arg Arg Ile Arg Ile Arg Arg
1               5                   10

<210> SEQ ID NO 49
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 49

Phe Ile Trp Arg Trp Arg Trp Arg
1               5

<210> SEQ ID NO 50
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 50

Pro Phe Trp Arg Trp Arg Ile Trp Arg
1               5

<210> SEQ ID NO 51
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 51

Pro Phe Trp Arg Ile Arg Ile Arg Arg
1               5

<210> SEQ ID NO 52

```
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 52

Pro Phe Trp Arg Gln Arg Ile Arg Arg
1               5

<210> SEQ ID NO 53
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 53

Pro Phe Trp Arg Ala Arg Ile Arg Arg
1               5

<210> SEQ ID NO 54
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 54

Pro Phe Trp Arg Lys Arg Ile Arg Arg
1               5

<210> SEQ ID NO 55
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 55

Pro Phe Trp Arg Lys Arg Leu Arg Arg
1               5

<210> SEQ ID NO 56
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 56

Pro Phe Trp Arg Lys Arg Trp Arg Arg
1               5

<210> SEQ ID NO 57
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 57

Pro Phe Trp Arg Arg Arg Ile Arg Arg
```

<210> SEQ ID NO 58
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 58

Pro Phe Trp Arg Arg Arg Trp Arg Arg
1               5

<210> SEQ ID NO 59
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 59

Pro Phe Trp Arg Ile Arg Ile Arg Arg Asp
1               5                   10

<210> SEQ ID NO 60
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 60

Pro Phe Phe Trp Arg Ile Arg Ile Arg Arg
1               5                   10

<210> SEQ ID NO 61
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 61

Pro Trp Arg Ile Arg Ile Arg Arg
1               5

<210> SEQ ID NO 62
<211> LENGTH: 12
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 62

Arg Phe Trp Gln Arg Asn Ile Arg Lys Val Arg Arg
1               5                   10

<210> SEQ ID NO 63
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity -continued

<400> SEQUENCE: 63

Arg Phe Trp Gln Arg Asn Ile Arg Lys Tyr Arg
1               5                   10

<210> SEQ ID NO 64
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 64

Pro Phe Trp Gln Arg Asn Ile Arg Lys Trp Arg
1               5                   10

<210> SEQ ID NO 65
<211> LENGTH: 13
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 65

Arg Phe Arg Trp Gln Arg Asn Ile Arg Lys Tyr Arg Arg
1               5                   10

<210> SEQ ID NO 66
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 66

Arg Trp Lys Arg Ile Asn Arg Gln Trp Phe
1               5                   10

<210> SEQ ID NO 67
<211> LENGTH: 7
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 67

Lys Arg Phe Cys Phe Lys Lys
1               5

<210> SEQ ID NO 68
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 68

Lys Arg Phe Ser Phe Lys Lys Cys
1               5

<210> SEQ ID NO 69
<211> LENGTH: 7
<212> TYPE: PRT

```
<213> ORGANISM: Artificial
<220> FEATURE:
<223> OTHER INFORMATION: Peptide exhibiting antimicrobial and/or
      endotoxin-neutralizing activity

<400> SEQUENCE: 69

Lys Arg Trp Ser Trp Lys Lys
1               5

<210> SEQ ID NO 70
<211> LENGTH: 7
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 70

Phe Arg Phe Ser Phe Lys Lys
1               5

<210> SEQ ID NO 71
<211> LENGTH: 7
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 71

Arg Arg Phe Trp Phe Arg Arg
1               5

<210> SEQ ID NO 72
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 72

Phe Trp Arg Asn Ile Arg Ile Arg Arg
1               5

<210> SEQ ID NO 73
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 73

Phe Trp Gln Arg Ile Arg Ile Arg Arg
1               5

<210> SEQ ID NO 74
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 74

Phe Trp Arg Trp Arg Ile Trp Arg
1               5
```

<210> SEQ ID NO 75
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 75

Phe Trp Arg Ile Arg Ile Arg Arg
1               5

<210> SEQ ID NO 76
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 76

Phe Trp Arg Asn Ile Arg Ile Trp Arg Arg
1               5                   10

<210> SEQ ID NO 77
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 77

Phe Trp Arg Asn Ile Arg Ile Arg Arg
1               5

<210> SEQ ID NO 78
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 78

Arg Phe Trp Gln Arg Asn Ile Arg Ile Arg Arg
1               5                   10

<210> SEQ ID NO 79
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 79

Arg Trp Gln Arg Asn Ile Arg Ile Arg Arg
1               5                   10

<210> SEQ ID NO 80
<211> LENGTH: 10
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 80

```
Arg Arg Ile Arg Ile Asn Arg Gln Trp Phe
1               5                   10

<210> SEQ ID NO 81
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 81

Pro Phe Trp Arg Arg Gln Ile Arg Arg
1               5

<210> SEQ ID NO 82
<211> LENGTH: 9
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 82

Pro Phe Trp Arg Lys Lys Leu Lys Arg
1               5

<210> SEQ ID NO 83
<211> LENGTH: 7
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 83

Pro Trp Arg Arg Ile Arg Arg
1               5

<210> SEQ ID NO 84
<211> LENGTH: 8
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 84

Pro Trp Arg Arg Lys Ile Arg Arg
1               5

<210> SEQ ID NO 85
<211> LENGTH: 11
<212> TYPE: PRT
<213> ORGANISM: Artificial
<220> FEATURE:
<223> OTHER INFORMATION: Peptide exhibiting antimicrobial and/or
      endotoxin-neutralizing activity

<400> SEQUENCE: 85

Pro Phe Trp Arg Arg Arg Ile Arg Ile Arg Arg
1               5                   10

<210> SEQ ID NO 86
<211> LENGTH: 7
<212> TYPE: PRT
<213> ORGANISM: Artificial
<220> FEATURE:
```

-continued

```
<223> OTHER INFORMATION: Peptide exhibiting antimicrobial and/or
      endotoxin-neutralizing activity

<400> SEQUENCE: 86

Arg Arg Trp Phe Trp Arg Arg
1               5

<210> SEQ ID NO 87
<211> LENGTH: 11
<212> TYPE: PRT
<213> ORGANISM: Artificial Sequence
<220> FEATURE:
<223> OTHER INFORMATION: Peptide exhibiting antimicrobial and/or
      endotoxin-neutralizing activity

<400> SEQUENCE: 87

Phe Gln Trp Gln Arg Asn Ile Arg Lys Val Arg
1               5                   10
```

ANTIMICROBIAL PEPTIDES

This application is a national phase application under 35 U.S.C. §371 of International Application No. PCT/AT2007/000345 filed 10 Jul. 2007, which claims priority to Austrian Application No. A 1165/2006 filed 10 Jul. 2006. The entire text of each of the above-referenced disclosures is specifically incorporated herein by reference without disclaimer.

The present invention relates to novel families of polypeptides and lipopolypeptides that have antimicrobial and endotoxin-neutralizing activities. The novel compounds can also be used in combination therapy with conventional antibiotics or antiendotoxic agents. In addition, the present invention discloses processes for making and using of the novel compounds.

The increasing occurrence of pathogenic bacteria that are resistant to commercially available antibiotics has led to a growing interest in the development of peptides as antibacterial drugs. Indeed, a large fraction of hospital-acquired infections (up to 70%) are now due to antibiotic-resistant bacteria. In addition to drug-resistance issues, antibiotic treatment for Gram-negative infections may cause release of endotoxin, which triggers septic shock, representing an additional challenge to anti-microbial therapy. Septic shock is the leading cause of mortality in intensive care units. Gram-negative bacteria in particular contain lipopolysaccharides (or LPS) in their envelope, which are the most potent elicitors of this response known. Moreover, antibiotics currently used for Gram-negative infections can kill bacteria, but the administration of antibiotics does not neutralize the LPS released from the outer membranes of the dying bacteria. This release of LPS can actually increase lung injury and lead to the septic syndrome. Therefore, agents that have antimicrobial properties and neutralize the released endotoxin would therefore be of great value to treat bacterial infection.

Since bacteria have evolved to present multiple resistance to a large number of existing antibiotics, new class of compounds are more likely to minimize the rapid emergence of bacterial resistance. Nature has taught us that effector molecules of mammalian innate immunity can provide a first line of defense against a substantial array of pathogenic microorganisms. In particular, host-defense peptides are considered to be multi-functional effector molecules and represent novel sources for the development of therapeutic agents with which to overcome antimicrobial resistance. While many conventional antibiotics damage or kill bacteria over a period of days, most antimicrobial peptides kill almost instantaneously, i.e. within minutes. A variety of antimicrobial peptides also block the interaction of LPS with its receptors such as LBP, CD14 and MD-2/TLR4, resulting in inhibition of activation of macrophages, a feature that may reduce LPS toxicity.

Lactoferrins are iron-binding endogenous glycoproteins found in exocrine secretions of mammals and in granules of neutrophils during inflammatory response that have antimicrobial and LPS binding activity. Lactoferrins exhibit multifunctional properties, which include antibacterial, antifungal, antiviral, antitumor, anti inflammatory, and immunoregulatory properties. Lactoferrin and derivatives are known to have the ability to neutralize bacterial endotoxin (LPS), thus protecting organisms from harmful effects of sepsis. Thus, the many reports on its antimicrobial and anti inflammatory activity in vitro identify lactoferrin as important in host defense against infection and excessive inflammation. In vitro and in vivo proteolytic digestion of human lactoferrin yields a peptide fragment called lactoferricin, which has enhanced antimicrobial activity compared to the integral lactoferrin. A number of shorter synthetic derivatives of lactoferricin exhibit antimicrobial activity against Gram positive and Gram negative bacteria and bind specifically to LPS (Strøm et al., *J. Peptide Res.* 57:127-139 (2001)). While many host defense peptides hold promise as novel antimicrobial candidates, human lactoferrin and derivatives are unique in that they possess multifunction activities and, due to their human origin, they are less likely to induce adverse physiological effects.

Myristoylated alanine-rich C kinase substrate (MARCKS) and MARCKS-related proteins are the major protein kinase C substrates in many cell types. Transcription of MARCKS was found to be significantly upregulated by stimulation of macrophages and microglial cells in response to bacterial LPS. The LPS-binding motif on MARCKS is very similar to potent antimicrobial hexapeptides identified using combinatorial library approaches. Since MARCKS is naturally modified by N-terminal myristoylation, one can anticipate that insertion of lipophilic groups into shorter MARCKS derivatives may result in potent antimicrobial activity and/or LPS binding.

The relevance of hydrophobicity and particularly of the presence of alkyl or acyl chains of lipopeptides for their antimicrobial activity has been described for lipopeptides (e.g., polymyxins, octapeptins and daptomycin). Furthermore, polymyxins have a high affinity for LPS molecules and permeabilize the outer membrane by disrupting the negatively charged head groups through displacement of divalent cations from their binding sites on LPS. Acylation of the N-terminus of a nonamer core peptide of lactoferricin B resulted in improved antimicrobial activities. Long-chain N-acyl amino acid antibiotics have recently been isolated from soil samples. Lipopolyamines (DOSPER, DOSPA, and DOGS, all containing a C17 alkyl chain) were also reported to exhibit anti-endotoxin activity by sequestering LPS and, in turn, by blocking downstream cellular activation events that lead to the production of proinflammatory mediators. Although ineffective when tested alone in neutropenic rats with invasive Gram-negative bacteremia caused by *Pseudomonas aeruginosa*, when administered with the antibiotic ceftazimidine, these lipopolyamines significantly increased the survival rate relative to ceftazimidine alone.

Ongoing developments of novel delivery systems are anticipated to increase the potential of peptides in the therapeutic field against infectious diseases. For instance, peptide delivery to brain tissue is now possible with the recent development of the chimeric peptide strategy (Bickel et al., *Adv. Drug Deliv. Rev.* 46:247-279 (2001)). A successful case of pneumonectomy and subsequent treatment with polymyxin B-immobilized fiber and continuous hemodiafiltration was reported to eliminate the causative factors of sepsis ("septic shock") in a patient suffering pulmonary turberculosis (Takahashi et al., *Ann. Thorac. Cardiovasc. Surg.* 9:319-322 (2003)). Similarly, to enhance the bioavailability of peptide drugs after oral administration, a number of strategies are under development. These include particulate drug delivery such as nanoparticles, microcapsules, liposomes or emulsions, mucoadhesive delivery, and the use of penetration enhancers (Kompella et al., *Adv. Drug Deliv. Rev.* 46:211-245 (2001)).

Japelj B. et al., (J Biol Chem. 280 (17) (2005): 16955-61) relates to an endotoxin-neutralizing peptide (LF11) comprising the amino acid sequence FQWQRNIRKVR-NH$_2$ (SEQ ID NO: 87) which is derived from lactoferrin. In the course of these studies, the amino acid residue of LF11, which is responsible for the LPS binding, was determined.

Comparable to Japelj B et al. also in Andrä J. et al. (Biochem J. 385 (2005): 135-43) the interaction of the lactoferrin derived peptide LF11, which was coupled to a C12-alkyl chain, to LPS was analysed.

In Farnaud S. et al. (FEMS Microbiol Lett. 238 (1) (2004): 221-6) antimicrobial peptides are disclosed which have been derived from bovine and human lactoferrin. The authors of this scientific work examined the binding of these peptides to LPS.

US 2003/0022821 A1 relates to modified lactoferrin peptides comprising 7 to 25 amino acid residues, whereby three or more of said amino acid residues are cationic. The peptides according to the US 2003/0022821 A1 further comprise a bulky and a lipophilic amino acid residue.

Chen P W et al. (Am J Vet Res. 64 (9) (2003): 1088-92) relates to lactoferrin analogues with a high content of lipophilic and cationic amino acid residues.

It is an object of the present invention to provide peptides exhibiting antimicrobial and endotoxin-neutralizing characteristics.

Therefore, the present invention relates to a peptide with antimicrobial or endotoxin-neutralizing activity having the formula:

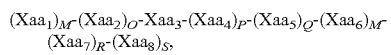
$(Xaa_1)_M\text{-}(Xaa_2)_O\text{-}Xaa_3\text{-}(Xaa_4)_P\text{-}(Xaa_5)_Q\text{-}(Xaa_6)_M\text{-}(Xaa_7)_R\text{-}(Xaa_8)_S$, wherein $Xaa_1$ is a hydrophobic amino acid, preferably selected from the group consisting of phenylalanine (Phe), alanine (Ala), leucine (Leu) and valine (Val), $Xaa_2$ is a basic amino acid, preferably selected from the group consisting of arginine (Arg) and lysine (Lys), $Xaa_3$ is a hydrophobic amino acid, preferably tryptophan (Trp), $Xaa_4$ is selected from the group consisting of alanine (Ala), arginine (Arg), glutamine (Gln), asparagine (Asn), proline (Pro), isoleucine (Ile), leucine (Leu) and valine (Val), $Xaa_5$ is selected from the group consisting of isoleucine (Ile), phenylalanine (Phe), tryptophan (Trp) and tyrosine (Tyr), $Xaa_6$ is selected from the group consisting of arginine (Arg), lysine (Lys), tyrosine (Tyr) and phenylalanine (Phe), $Xaa_7$ is a hydrophobic amino acid, preferably selected from the group consisting of isoleucine (Ile), tryptophan (Trp), valine (Val) and leucine (Leu), and $Xaa_8$ is selected from the group consisting of arginine (Arg), lysine (Lys), isoleucine (Ile) and serine (Ser), and wherein O is 0, M is 1 or 2, P is 2 or 3, Q and R are 1, and S is 1, 2, 3 or 4.

The present invention relates to isolated peptides, polypeptides and lipopeptides that exhibit antimicrobial activity and endotoxin-neutralizing activity. These molecules show a broad spectrum of activity against various pathogens (including bacteria, viruses, fungi etc.). Development of active compounds was based on the SAR analysis, biophysical, microbiological, immunological and structural experiments using novel peptide compounds.

This invention provides peptides and lipopeptides having antimicrobial and/or antiendotoxic activity. As used herein, the term "amino acid" refers both to the naturally occurring amino acids and their derivatives. In addition, a mimic of one or more amino acids, otherwise known as peptide mimetic or peptidomimetic can also be used. As used herein, the term "mimic" means an amino acid or an amino acid analog that has the same or similar functional characteristic of an amino acid. A peptide mimetic or peptidomimetic is an organic molecule that retains similar peptide chain pharmacophore groups as are present in the corresponding peptide. The substitution of amino acids by non-naturally occurring amino acids or peptidomimetics as described above can enhance the overall activity or other properties of an individual peptide based on the modifications of the side chain functionalities. For example, these types of modifications to the exemplified peptides can enhance the peptide's stability to enzymatic breakdown or increase biological activity or decrease immunogenicity.

One skilled in the art can easily synthesize the peptides and lipopeptides of this invention. Standard procedures for preparing synthetic peptides are well known in the art. Peptides of the invention can be synthesized by such commonly used methods as t-BOC or FMOC protection of alpha-amino groups. Both methods involve stepwise syntheses whereby a single amino acid is added at each step starting from the carboxyl-terminus of the peptide (See, Coligan et al., Current Protocols in Immunology, Wiley Interscience, 1991, Unit 9). Peptides of the invention can also be synthesized by the solid phase peptide synthesis methods well known in the art. (Merrifield, J. Am. Chem. Soc., 85:2149, 1963), and Stewart and Young, Solid Phase Peptides Synthesis, Pierce, Rockford, Ill. (1984)). Peptides can be synthesized using a copoly(styrenedivinylbenzene) containing 0.1-1.0 mMol amines/g polymer. On completion of chemical synthesis, the peptides can be deprotected and cleaved from the polymer by treatment with liquid HF-10% anisole for about 0.25 to 1 hour at 0° C. After evaporation of the reagents, the peptides are extracted from the polymer with 1% acetic acid solution which is then lyophilized to yield the crude material. This can typically be purified by such techniques as gel filtration on Sephadex G-15 using 5% acetic acid as a solvent, by high pressure liquid chromatography, and the like. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and assessed by the solid phase Edman degradation (see e.g Protein Purification, M. P. Deutscher, ed. Methods in Enzymology, Vol 182, Academic Press, 1990). Automated synthesis using FMOC solid phase synthetic methods can be achieved using an automated peptide synthesizer (Model 432A, Applied Biosystems, Inc.).

The peptides/polypeptides of the present invention can also be synthesized using a fusion protein microbial method in which an anionic carrier peptide is fused to a cationic peptide. A method for such microbial production of cationic peptides having anti-microbial activity is provided in U.S. Pat. No. 5,593,866.

The peptide of the present invention thus produced can be purified by isolation/purification methods for proteins generally known in the field of protein chemistry. More particularly, there can be mentioned, for example, extraction, recrystallization, salting out with ammonium sulfate, sodium sulfate, etc., centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, etc. and combinations of these. Most effective is a method by reversed-phase high performance liquid chromatography.

The peptide of the present invention may form a salt by addition of an acid. Examples of the acid include inorganic acids (such as trifluoroacetic acid, hydrochloric acid, hydrobromic acid, phosphoric acid, nitric acid, and sulfuric acid) or organic carboxylic acids (such as acetic acid, propionic acid, maleic acid, succinic acid, malic acid, citric acid, tartaric acid, and salicylic acid), acidic sugars such as glucuronic acid, galacturonic acid, gluconic acid, ascorbic acid, etc., acidic polysaccharides such as hyaluronic acid, chondroitin sulfates, alginic acid, or organic sulfonic acids (such as methanesulfonic acid, and p-toluenesulfonic acid), and the like. Of these salts, preferred is a pharmaceutically acceptable salt.

The peptide of the present invention may form a salt with a basic substance. Examples of the salt include, for example, pharmaceutically acceptable salts selected from salts with inorganic bases such as alkali metal salts (sodium salt, lithium salt, potassium salt etc.), alkaline earth metal salts, ammonium salts, and the like or salts with organic bases, such as diethanolamine salts, cyclohexylamine salts and the like.

The term "amino acid" used herein means an L-amino acid. However, also D-amino acids may be employed in the manufacturing of the peptides according to the present invention.

"Peptides", as used herein, comprise 2 to 50 amino acid residues. "Polypeptides" and "proteins" comprise more than 50 amino acid residues.

"Antimicrobial", as used herein, refers to the biological activity of the peptides and polypeptides of the present invention, and means that the peptide/polypeptide has the capacity to kill, disrupt reproduction or otherwise disable microbial growth so that the polypeptide has a minimal inhibitory concentration ("MIC" as determined in Mueller Hinton medium following recommendations of the Clinical and Laboratory Standards Institute, CLSI—formerly NCCLS—) of less than 32 µM, preferably less than 16 µM. Microbes to be inhibited according to the present invention include bacteria, fungi, yeast, etc. The procedures for determining MIC of an antimicrobial polypeptide are known to those skilled in the art and are described, for instance, in Powell et al. (Molecular Plant-Microbe Interactions, 8:792-794 (1995)), Wu and Hancock (J. Biol. Chem. 274:29-35 (1999)) and Lorian V. ("Antimicrobials in laboratory Medicine", 1996 4$^{th}$ ed. pp. 330-396, Williams and Wilkins, Baltimore, Md.). A MIC assay allows the determination of the lowest concentration of peptide that inhibits the multiplication and growth of microorganisms. It is contemplated that, for purposes of the present invention, a polypeptide is an antimicrobial if it has the aforementioned MIC with respect to a microorganism as used herein.

The "endotoxin-neutralizing" and/or binding activity of the peptides of the present invention may be tested in an in vitro assay using, for instance, a macrophage cell line (Gough et al. (1996) Infect. Immun. 64:4922-4927).

The peptides according to the present invention show also antifungal activity. This activity was shown for several fungi, for instance for *cryptococcus neoformans*.

The formula comprises preferably an amino acid sequence selected from the group consisting of FWQRIRKVR (SEQ ID No. 1), FWQRRIRKVRR (SEQ ID No. 2), FWQRKIRKVRK (SEQ ID No. 3), FWQRNIRIRR (SEQ ID No. 4), FWQRNIRKVR (SEQ ID No. 5), FWQRNIRVR (SEQ ID No. 6), FWQRNIRKVRR (SEQ ID No. 7), FWQRNIRKVKK (SEQ ID No. 8), FWQRNIRKVRRR (SEQ ID No. 9), FWQRNIRKVKKK (SEQ ID No. 10), FWQRNIRKVRRRR (SEQ ID No. 11), FWQRNIRKVRRRI (SEQ ID No. 12), FWQRNIRKVKKKK (SEQ ID No. 13), FWQRNIRKVKKKI (SEQ ID No. 14), FWQRNIRKIR (SEQ ID No. 15), FWQRNIRKLR (SEQ ID No. 16), FWQRNIRKWR (SEQ ID No. 17), FWQRNRWRKVR (SEQ ID No. 18), FWQRNFRKVR (SEQ ID No. 19), FWQRNYRKVR (SEQ ID No. 20), FWQRNIRKVS (SEQ ID No. 21), FWQRRIRIRR (SEQ ID No. 22), FWQRPIRKVR (SEQ ID No. 23), FWQRRIRKWR (SEQ ID No. 24), FWQRRIRRWRR (SEQ ID No. 25), FWPRNIRKVR (SEQ ID No. 26), FWARNIRKVR (SEQ ID No. 27), FWIRNIRKVR (SEQ ID No. 28), FWLRNIRKVR (SEQ ID No. 29), FWVRNIRKVR (SEQ ID No. 30), FWQRNIFKVR (SEQ ID No. 31), FWQRNIYKVR (SEQ ID No. 32), FAWQRNIRKVR (SEQ ID No. 33), FLWQRNIRKVR (SEQ ID No. 35) and FVWQRNIRKVR (SEQ ID No. 36).

As used in the present invention small letters in amino acid sequences mean that these specific amino acid residues are of the D-configuration and not of the L-configuration (capital letters).

Another aspect of the present invention relates to a peptide with antimicrobial or endotoxin-neutralizing activity having the formula:

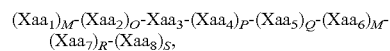

wherein

Xaa$_1$ is a hydrophobic amino acid, preferably selected from the group consisting of phenylalanine (Phe) and isoleucine (Ile), Xaa$_2$ is a basic amino acid, preferably selected from the group consisting of arginine (Arg), lysine (Lys), Xaa$_3$ is a hydrophobic amino acid, preferably tryptophan (Trp), Xaa$_4$ is selected from the group consisting of glycine (Gly), asparagine (Asn), isoleucine (Ile) and phenylalanine (Phe), Xaa$_5$ is isoleucine (Ile) or tryptophan (Trp), Xaa$_6$ is arginine (Arg) or lysine (Lys), Xaa$_7$ is a hydrophobic amino acid, preferably selected from the group consisting of isoleucine (Ile), tryptophan (Trp) and valine (Val) and Xaa$_8$ is arginine (Arg), and wherein O is 0, M is 1 or 2, R is 0 or 1, P is 1, 2 or 3, Q is 1, and S is 0, 1 or 2.

The formula comprises preferably an amino acid sequence selected from the group consisting of FWRIRKWR (SEQ ID No. 37), FWRIRKVR (SEQ ID No. 38), FWRWRR (SEQ ID No. 39), FWRRWRR (SEQ ID No. 40), FWRRWIRR (SEQ ID No. 41), FWRGWRIRR (SEQ ID No. 42), FWRRFWRR (SEQ ID No. 43), FWRWRWR (SEQ ID No. 44), FWRIWRWR (SEQ ID No. 45), FWRIWRIWR (SEQ ID No. 46), FWRNIRKWR (SEQ ID No. 47) and FWRRRIRIRR (SEQ ID No. 48).

Another aspect of the present invention relates to a peptide with antimicrobial or endotoxin-neutralizing activity having the formula:

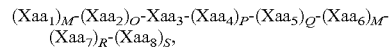

wherein

Xaa$_1$ is a hydrophobic amino acid, preferably selected from the group consisting of proline (Pro) and phenylalanine (Phe), Xaa$_2$ is a basic amino acid, preferably selected from the group consisting of arginine (Arg), lysine (Lys)

Xaa$_3$ is a hydrophobic amino acid, preferably tryptophan (Trp),

Xaa₄ is selected from the group consisting of alanine (Ala), arginine (Arg), glutamine (Gln), lysine (Lys), tryptophan (Trp) and isoleucine (Ile), Xaa₅ is selected from the group consisting of isoleucine (Ile) and tryptophan (Trp), Xaa₆ is selected from the group consisting of arginine (Arg) and aspartate (Asp), Xaa₇ is a hydrophobic amino acid, preferably selected from the group consisting of isoleucine (Ile), tryptophan (Trp), phenylalanine (Phe), valine (Val) and leucine (Leu), and Xaa₈ is selected from the group consisting of arginine (Arg), lysine (Lys), isoleucine (Ile), serine (Ser) and aspartate (Asp), and wherein O and Q are 0,
M is 0, 1, 2 or 3,
R is 1 or 2,
P is 1, 2 or 3, and
S is 1, 2 or 3.

The formula comprises preferably an amino acid sequence selected from the group consisting of PFWRWRIWR (SEQ ID No. 50), PFWRIRIRR (SEQ ID No. 51), PFWRQRIRR (SEQ ID No. 52), PFWRARIRR (SEQ ID No. 53), PFWRKRIRR (SEQ ID No. 54), PFWRKRLRR (SEQ ID No. 55), PFWRKRWRR (SEQ ID No. 56), PFWRRRIRR (SEQ ID No. 57), PFWRRRWRR (SEQ ID No. 58), PFWR-IRIRRD (SEQ ID No. 59), PFFWRIRIRR (SEQ ID No. 60), PWRIRIRR (SEQ ID No. 61), PFWRRQIRR (SEQ ID No. 81), PFWRKKLKR (SEQ ID No. 82), PWRRIRR (SEQ ID No. 83), PWRRKIRR (SEQ ID No. 84) and PFWRRIRIRR (SEQ ID No. 85).

Yet another aspect of the present invention relates to a peptide with antimicrobial or endotoxin-neutralizing activity having the formula:

$(Xaa_1)_M\text{-}(Xaa_2)_O\text{-}Xaa_3\text{-}(Xaa_4)_P\text{-}(Xaa_5)_Q\text{-}(Xaa_6)_M\text{-}(Xaa_7)_R\text{-}(Xaa_8)_S,$ wherein Xaa₁ is a hydrophobic amino acid, preferably selected from the group consisting of proline (Pro) and phenylalanine (Phe), Xaa₂ is a basic amino acid, preferably arginine (Arg), Xaa₃ is a hydrophobic amino acid, preferably tryptophan (Trp), Xaa₄ is selected from the group consisting of alanine (Ala), arginine (Arg), glutamine (Gln), asparagine (Asn) and lysine (Lys), Xaa₅ is selected from the group consisting of isoleucine (Ile), phenylalanine (Phe) and tryptophan (Trp), Xaa₆ is selected from the group consisting of glutamine (Gln), arginine (Arg) and asparagine (Asn), Xaa₇ is a hydrophobic amino acid, preferably selected from the group consisting of isoleucine (Ile), tryptophan (Trp) and phenylalanine (Phe), and Xaa₈ is arginine (Arg), and wherein M is 0, 1, 2 or 3,
O is 0 or 1,
P is 1, 2 or 3,
Q is 1 or 2, and
R and S are 0, 1 or 2.

The formula comprises preferably an amino acid sequence selected from the group consisting of FWRNIRIRR (SEQ ID No. 72), FWQRIRIRR (SEQ ID No. 73), FWRWRIWR (SEQ ID No. 74), FWRIRIRR (SEQ ID No. 75), FWRNIRI-WRR (SEQ ID No. 76) and FwRNIRIRR (SEQ ID No. 77).

Another aspect of the present invention relates to a peptide with antimicrobial or endotoxin-neutralizing activity having a formula comprising an amino acid sequence selected from the group consisting of RFWQRNIRKVRR (SEQ ID No. 62), RFWQRNIRKYR (SEQ ID No. 63), PFWQRNIRKWR (SEQ ID No. 64), RFRWQRNIRKYRR (SEQ ID No. 65), RWKRINRQWF (SEQ ID No. 66), KRFCFKK (SEQ ID No. 67), KRFSFKKC (SEQ ID No. 68), KRWSWKK (SEQ ID No. 69), FRFSFKK (SEQ ID No. 70), RRFWFRR (SEQ ID No. 71), RFWQRNIRIRR (SEQ ID No. 78), RWQRNIRIRR (SEQ ID No. 79) and RRWFWRR (SEQ ID No. 86).

Another aspect of the present invention relates to a peptide with antimicrobial or endotoxin-neutralizing activity having the formula FIWQRNIRKVR (SEQ ID No. 34), FIWR-WRWR (SEQ ID No. 49) and RRIRINRQWF (SEQ ID No. 80).

The N- and/or C-terminus of the peptides according to the present invention may have modifications, such as ac(et)ylation, amidations, esterifications, reductions, oxidations, (co-valent) linker binding, peptide bonds, disulfide bonds, etc. The peptides may further be modified, e.g. by carbohydrates, linker molecules, lipids, etc.

The C-terminus of the peptides according to the present invention consists preferably of a group selected from the group consisting of carboxyl group, amide groups, in particular consisting of a N-methylamido group, esther, ether or ketone, preferably comprising from 1 to 20 carbon atoms, more preferably from 1 to 10 carbon atoms.

According to a preferred embodiment of the present invention an acyl group is bound to the N-terminus or C-terminus of the peptide.

In order to increase the hydrophobicity of the peptides according to the present invention and consequently to increase the interaction of the peptides with, for instance, hydrophobic parts of cells (e.g. cell membrane), the peptides are preferably modified with acyl groups.

The acyl group to be bound to the peptides according to the present invention is preferably a hydrophobic chain selected from the group consisting of saturated and unsaturated linear and branched acyl chains of $C_2$-$C_{20}$, benzyl-derivatives and F-moc.

The acyl group is preferably selected from the group consisting of Dodecanoyl-group, Decanoyl-group, Octanoyl-group, Hexanoyl-group, 2-Methylhexanoyl-group, 2-Ethylhexanoyl-group, 2-Propylpentanoyl-group, 2-Butyloctanoyl-group, 2,2-dimethylbutanoyl-group, 2-methylpentanoyl-group, 3-methylpentanoyl-group, 4-methylpentanoyl-group, 6-methyloctanoyl-group, Benzyl-group and dicyclohexylacetyl-group.

Particularly preferred modified or unmodified peptides according to the present invention can be found in Table 1.

TABLE 1

Peptides according to the present invention

| SEQ ID NO. | Peptide Des. | C-terminal modification | Amino Acid sequence | |
|---|---|---|---|---|
| 1 | | | F W Q R  I R K V R | —NH₂ |
| 2 | P15 | | F W Q R R I R K V R R | —NH₂ |

TABLE 1-continued

Peptides according to the present invention

| SEQ ID NO. | Peptide Des. | C-terminal modification | Amino Acid sequence | |
|---|---|---|---|---|
| 3 | P2-1 | | `F W Q R K I R K V R K` | —NH₂ |
| 4 | VS1-13 | | `F W Q R N I R     I R R` | —NH₂ |
| 5 | | | `F W Q R N I R K V R` | —NH₂ |
| 6 | | | `F W Q R N I R   V R` | —NH₂ |
| 7 | | | `F W Q R N I R K V R R` | —NH₂ |
| 8 | | | `F W Q R N I R K V K K` | —NH₂ |
| 9 | | | `F W Q R N I R K V R R R` | —NH₂ |
| 10 | | | `F W Q R N I R K V K K K` | —NH₂ |
| 11 | | | `F W Q R N I R K V R R R R` | —NH₂ |
| 12 | P1-12 | | `F W Q R N I R K V R R R I` | —NH₂ |
| 13 | | | `F W Q R N I R K V K K K K` | —NH₂ |
| 14 | | | `F W Q R N I R K V K K K I` | —NH₂ |
| 15 | | | `F W Q R N I R K I R` | —NH₂ |
| 16 | | | `F W Q R N I R K L R` | —NH₂ |
| 17 | VS1-15 | | `F W Q R N I R K W R` | —NH₂ |
| 18 | | | `F W Q R N W R K V R` | —NH₂ |
| 19 | | | `F W Q R N F R K V R` | —NH₂ |
| 20 | P1-39 | | `F W Q R N Y R K V R` | —NH₂ |
| 21 | | | `F W Q R N I R K V S` | —NH₂ |
| 22 | | | `F W Q R R I R     I R R` | —NH₂ |
| 23 | | | `F W Q R P I R K V R` | —NH₂ |
| 24 | VS1-17 | | `F W Q R R I R K W R` | —NH₂ |
| 25 | VS1-18 | | `F W Q R R I R R W R R` | —NH₂ |
| 26 | | | `F W P R N I R K V R` | —NH₂ |
| 27 | | | `F W A R N I R K V R` | —NH₂ |
| 28 | | | `F W I R N I R K V R` | —NH₂ |
| 29 | | | `F W L R N I R K V R` | —NH₂ |
| 30 | | | `F W V R N I R K V R` | —NH₂ |
| 31 | | | `F W Q R N I F K V R` | —NH₂ |
| 32 | P41 | | `F W Q R N I Y K V R` | —NH₂ |
| 33 | | | `F A W Q R N I R K V R` | —NH₂ |
| 34 | | | `F I W Q R N I R K V R` | —NH₂ |
| 35 | | | `F L W Q R N I R K V R` | —NH₂ |
| 36 | | | `F V W Q R N I R K V R` | —NH₂ |
| 37 | VS1-21 | | `F W   R     I R K   W R` | —NH₂ |
| 38 | | | `F W   R     I R K   V R` | —NH₂ |
| 39 | | | `F W   R     W         R R` | —NH₂ |

TABLE 1-continued

Peptides according to the present invention

| SEQ ID NO. | Peptide Des. | C-terminal modification | Amino Acid sequence |
|---|---|---|---|
| 40 | P2-24 | | F W   R R       W           R R   —NH$_2$ |
| 41 | P2-25 | | F W   R R       W I         R R   —NH$_2$ |
| 42 | P2-26 | | F W   R     G W R     I R R       —NH$_2$ |
| 43 | P2-27 | | F W   R R   F W R       R         —NH$_2$ |
| 44 | P2-28 | | F W   R       W R       W R       —NH$_2$ |
| 45 | P2-29 | | F W   R     I W R       W R       —NH$_2$ |
| 46 | P2-31 | | F W   R     I W R     I W R       —NH$_2$ |
| 47 | VS1-20 | | F W   R     N I R K     W R       —NH$_2$ |
| 48 | | | F W   R R R I       R I     R R   —NH$_2$ |
| 49 | P2-32 | | F I W   R       W   R     W R     —NH$_2$ |
| 50 | P2-33 | | P F   W R     W       R I W R     —NH$_2$ |
| 51 | VS1-22 | | P F   W R     I       R I   R R   —NH$_2$ |
| 52 | VS1-25 | | P F   W R     Q       R I   R R   —NH$_2$ |
| 53 | VS1-27 | | P F   W R     A       R I   R R   —NH$_2$ |
| 54 | VS1-28 | | P F   W R K             R I   R R   —NH$_2$ |
| 55 | VS1-29 | | P F   W R K             R L   R R   —NH$_2$ |
| 56 | VS1-31 | | P F   W R K             R W   R R   —NH$_2$ |
| 57 | VS1-32 | | P F   W R R             R I   R R   —NH$_2$ |
| 58 | VS1-33 | | P F   W R R             R W   R R   —NH$_2$ |
| 59 | VS1-23 | | P F   W R     I       R I   R R D —NH$_2$ |
| 60 | VS1-24 | | P F F W R     I       R I   R R   —NH$_2$ |
| 61 | VS1-34 | | P     W R     I       R I   R R   —NH$_2$ |
| 62 | | | R F   W Q R N I R K V R R         —NH$_2$ |
| 63 | | | R F   W Q R N I R K Y R           —NH$_2$ |
| 64 | VS1-19 | | P F   W Q R N I R K W R           —NH$_2$ |
| 65 | P22 | | R F R W Q R N I R K Y R R         —NH$_2$ |
| 66 | VS1-16 | | R     W K R I N     R Q W F       —NH$_2$ |
| 67 | P60 | | K R F C F K K                     —NH$_2$ |
| 68 | | | K R F S F K K c                   —NH$_2$ |
| 69 | P1-63 | | K R W S W K K                     —NH$_2$ |
| 70 | | | F R F S F K K                     —NH$_2$ |
| 71 | P2-55 | | R R F W F R R                     —NH$_2$ |
| 72 | P2-10 | |         F W   R N I R I R R       —NH$_2$ |
| 73 | P2-13 | |         F W Q R     I R I R R     —NH$_2$ |
| 74 | P2-30 | | F W   R       W R I W     R       —NH$_2$ |
| 75 | P2-15 | | F W   R     I R I     R R         —NH$_2$ |
| 75 | VF50 | cyclo | F W   R     I R I     R R         —NH$_2$ |

TABLE 1-continued

Peptides according to the present invention

| SEQ ID NO. | Peptide Des. | C-terminal modification | Amino Acid sequence | |
|---|---|---|---|---|
| 76 | P2-16 | | F W   R N   I R I W R R | —NH₂ |
| 77 | P2-11 | | F w   R N   I R I   R R | —NH₂ |
| 78 | P2-18 | | R F W Q R N   I R I   R R | —NH₂ |
| 79 | P2-19 | | R   W Q R N   I R I   R R | —NH₂ |
| 80 | VS1-14 | | R R I R I N R Q W F | —NH₂ |
| 81 | VS1-26 | | P F W R R Q I R R | —NH₂ |
| 82 | VS1-30 | | P F W R K K L K R | —NH₂ |
| 83 | VS1-35 | | P W R R I R R | —NH₂ |
| 84 | VS1-36 | | P W R R K I R R | —NH₂ |
| 85 | VS1-37 | | P F W R R R I R I R R | —NH₂ |
| 86 | VS1-39 | | R R W F W R R | -OH |
| 4 | | Fmoc- | F W Q R N I R I R R | —NH₂ |
| 72 | | Fmoc- | F W   R N I R I R R | —NH₂ |
| 73 | | Fmoc- | F W Q R   I R I R R | —NH₂ |
| 4 | | Lauryl- | F W Q R N I R I R R | —NH₂ |
| 4 | | Decanoyl- | F W Q R N I R I R R | —NH₂ |
| 4 | | Octanoyl- | F W Q R N I R I R R | —NH₂ |
| 4 | | Hexanoyl- | F W Q R N I R I R R | —NH₂ |
| 4 | | 2-Methylhexanoyl- | F W Q R N I R I R R | —NH₂ |
| 4 | | 2-Ethylhexanoyl- | F W Q R N I R I R R | —NH₂ |
| 4 | | 2-Propyl-pentanoyl- | F W Q R N I R I R R | —NH₂ |
| 4 | | 2-Butyloctanoyl- | F W Q R N I R I R R | —NH₂ |
| 4 | | 2,2-dimethyl-butanoyl- | F W Q R N I R I R R | —NH₂ |
| 4 | | 2-methyl-pentanoyl- | F W Q R N I R I R R | —NH₂ |
| 4 | | 3-methyl-pentanoyl- | F W Q R N I R I R R | —NH₂ |
| 4 | | 4-methyl-pentanoyl- | F W Q R N I R I R R | —NH₂ |
| 4 | P2-51 | 6-methyl-octanoyl- | F W Q R N I R I R R | —NH₂ |
| 4 | | Benzyl- | F W Q R N I R I R R | —NH₂ |
| 17 | VS1-40 | octanoyl | F W Q R N I R K W R | —NH₂ |
| 17 | VS1-41 | 2-ethylhexanoyl | F W Q R N I R K W R | —NH₂ |
| 17 | VS1-42 | 2,2-dimethyl-butanoyl | F W Q R N I R K W R | —NH₂ |

TABLE 1-continued

Peptides according to the present invention

| SEQ ID NO. | Peptide Des. | C-terminal modification | Amino Acid sequence | |
|---|---|---|---|---|
| 17 | VS1-43 | 6-methyl-octanoyl | F W Q R N I R K W R | —NH$_2$ |
| 17 | VS1-44 | dicyclohexyl-acetyl | F W Q R N I R K W R | —NH$_2$ |
| 66 | VS1-45 | octanoyl | R W K R I N R Q W F | —NH$_2$ |
| 66 | VS1-46 | 2-ethylhexanoyl | R W K R I N R Q W F | —NH$_2$ |
| 66 | VS1-47 | 2,2-dimethyl-butanoyl | R W K R I N R Q W F | —NH$_2$ |
| 66 | VS1-48 | 6-methyl-octanoyl | R W K R I N R Q W F | —NH$_2$ |
| 66 | VS1-49 | dicyclohexyl-acetyl | R W K R I N R Q W F | —NH$_2$ |
| 51 | VS1-50 | octanoyl | P F W R I R I R R | —NH$_2$ |
| 51 | VS1-51 | 2-ethylhexanoyl | P F W R I R I R R | —NH$_2$ |
| 51 | VS1-52 | 2,2-dimethyl-butanoyl | P F W R I R I R R | —NH$_2$ |
| 51 | VS1-53 | 6-methyl-octanoyl | P F W R I R I R R | —NH$_2$ |
| 51 | VS1-54 | dicyclohexyl-acetyl | P F W R I R I R R | —NH$_2$ |
| 75 | VS1-55 | octanoyl | F W R I R I R R | —NH$_2$ |
| 75 | VS1-56 | 2-ethylhexanoyl | F W R I R I R R | —NH$_2$ |
| 75 | VS1-57 | 2,2-dimethyl-butanoyl | F W R I R I R R | —NH$_2$ |
| 75 | VS1-58 | 6-methyl-octanoyl | F W R I R I R R | —NH$_2$ |
| 75 | VS1-59 | dicyclohexyl-acetyl | F W R I R I R R | —NH$_2$ |
| 43 | VS1-60 | octanoyl | F W R R F W R R | —NH$_2$ |
| 43 | VS1-61 | 2-ethylhexanoyl | F W R R F W R R | —NH$_2$ |
| 43 | VS1-62 | 2,2-dimethyl-butanoyl | F W R R F W R R | —NH$_2$ |
| 43 | VS1-63 | 6-methyl-octanoyl | F W R R F W R R | —NH$_2$ |
| 43 | VS1-64 | dicyclohexyl-acetyl | F W R R F W R R | —NH$_2$ |

Another aspect of the present invention relates to a polypeptide comprising a peptide according to the present invention.

The peptides of the present invention may also be part of a polypeptide provided that the (non naturally occurring) polypeptide comprising said peptide(s) exhibits the same antimicrobial and/or endotoxin-neutralizing activities. However the fusion polypeptide may exhibit lower or even higher activity than the peptide.

Various peptides according to the present invention may also be linked/fused to each other in order to form new peptides or polypeptides. The same applies for the use of the peptides according to the present invention as repeating units in order to obtain peptides or polypeptides with two, three, four, five, ten or 20 repeating units.

Another aspect of the present invention relates to a pharmaceutical composition comprising a peptide or polypeptide according to the present invention.

Such a composition can be used to treat and/or prevent, e.g., microbial infection or septic shock. Finally, the present invention relates to a method of co-administrating a polypeptide or lipopeptide from this invention with other antimicrobial or anti-septic agents in a pharmaceutical acceptable carrier or inert substance to improve the efficiency of the said other anti-microbial or anti-septic agents.

According to a preferred embodiment of the present invention the composition comprises further at least one additional anti-microbial or anti-septic agent.

In order to obtain a pharmaceutical composition with even better antimicrobial and/or endotoxin-neutralizing effects additional agents exhibiting similar properties as the peptides according to the present invention are added. Of course it is also possible to add agents with activities other than the peptides according to the present invention. These substances may be helpful in increasing the bioavailability such as for example increasing the stability of the peptides or their delivery.

Examples of particular agents which may be combined with the peptides of the invention include aminoglycosides (e.g., tobramycin), penicillins (e.g., piperacillin), cephalosporins (e.g., ceftazidime), fluoroquinolones (e.g., ciprofloxacin), carbepenems (e.g., imipenem), tetracyclines and macrolides (e.g., erythromycin and clarithromycin). The composition may further include the addition of antibiotics for combination or synergistic therapy. The appropriate antibiotic administered will typically depend on the susceptibility of the microorganism such as whether, e.g., the bacteria is Gram-negative or Gram-positive, and will be easily discernable by one of skill in the art. Further to the antibiotics listed above, typical antibiotics include amino-glycosides (amikacin, gentamicin, kanamycin, netilmicin, tobramycin, streptomycin, azithromycin, clarithromycin, erythromycin, erythromycin estolate/ethylsuccinate/gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin.

The composition according to the present invention may preferably further comprise a pharmaceutically acceptable excipient.

The pharmaceutical composition of the present invention may consist of the peptide of the present invention alone or may be in the form of a composition comprising the peptide of the present invention and a pharmaceutically acceptable carrier. The pharmaceutically acceptable carrier which can be used is not limited particularly and includes an excipient, a binder, a lubricant, a colorant, a disintegrant, a buffer, an isotonic agent, a preservative, an anesthetic, and the like which can be used in a medical field. Also, it may be used in combination with another antimicrobial medicine such as lysozyme, antibiotics, and the like.

The composition of the present invention can be used for the treatment of, for example, the part infected with microorganisms outside the body or for the treatment of microbial infection inside the body, and an appropriate administration method therefore can be selected depending on the purpose of treatment, from injection (subcutaneous, intracutaneous, intravenous, intraperitoneal, etc.), eye dropping, instillation, percutaneous administration, oral administration, inhalation, etc.

Also, the dosage form such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointment, suppositories, pessaries, and the like can be appropriately selected depending on the administration method, and the antimicrobial medicine of the present invention can be accordingly formulated.

Another aspect of the present invention relates to the use of a peptide or polypeptide according to the present invention as antimicrobial or as endotoxin-neutralizing agent.

The peptides disclosed herein exhibit antimicrobial and/or endotoxin-neutralizing activities. Therefore these peptides may be suitably employed either as antimicrobial agent or as an agent neutralizing endotoxin.

Another aspect of the present invention relates to the use of a peptide or polypeptide according to the present invention for manufacturing a medicament for treating or preventing infections caused by microorganisms, preferably by bacteria, or sepsis or septic shock caused preferably by endotoxins.

Due to their biological characteristics the peptides of the present invention are suitably employed in medicaments.

According to a preferred embodiment of the present invention the medicament may preferably further comprise at least one additional antimicrobial or anti-septic agent.

The medicament further comprises preferably a pharmaceutically acceptable excipient.

Another aspect of the present invention relates to a method of inhibiting the growth of at least one microorganism comprising the step of contacting said microorganism with an effective amount of a peptide or polypeptide according to the present invention.

The peptides and polypeptides of the present invention may be used to inhibit the growth of microorganisms. This effect may be achieved by contacting said molecules with the microorganisms to be inhibited.

As used herein, the term "therapeutically effective amount" or "effective amount" for inhibiting the growth of a microorganism refers to the amount of peptide which is sufficient to decrease the subject's response to LPS and decrease the symptoms of sepsis. The term "therapeutically effective" therefore includes that the amount of peptide sufficient to prevent, and preferably reduce by at least 50%, and more preferably sufficient to reduce by 90%, a clinically significant increase in the plasma level of TNF. The dosage ranges for the administration of peptide are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

According to a preferred embodiment of the present invention said microorganism is a Gram-positive or Gram-negative bacterium.

The peptides and polypeptides disclosed herein are in particular effective against bacteria. Therefore the preferred microorganism to be contacted with are preferably of the family of enterobactericeae, in particular *Escherichia coli*, *Salmonella* spp., *Yersinia pestis*, *Yersinia enterocolitica* or *Klebsiella* spp., preferably of the family of pseudomonadaceae, in particular *Pseudomonas aeruginosa*, preferably of the family of alcaligenaceae, in particular *Bordetella bronchiseptica* or *Bordetella pertussis*, preferably of the family of brucellaceae, in particular *Brucella abortus*, preferably of the family of moraxellaceae, in particular *Acinetobacter baumanii*, preferably of the family of xanthononadaceae, in particular *Stenotrophomonas maltophilia*, preferably of the family of pasteuerellaceae, in particular *Haemophilus Influenzae*, preferably of the family of neisseriaceae, in particular *Neisseria meningitidis*, preferably of the family of staphylococcaceae, in particular *Staphylococcus aureus* or *Staphylococcus epidermidis*, preferably of the family of enterococcaceae, in particular *Enterococcus faecalis*, preferably of the family of streptococcaceae, in particular *Streptococcus agalactiae* and preferably of the family of chlamydiaceae, in particular *Chlamydia pneumoniae*.

The use of the peptides according to the present invention is especially suited if said microorganism exhibits multiple drug resistance.

Multiple drug resistance (i.e. resistance of microorganisms against a number of drugs, in particular of antibiotics) is one of the major problems in clinical practice. Therefore, it is important to provide new agents which may affect the growth of microorganisms.

Another aspect of the present invention relates to a method of neutralizing the biological activity of bacterial components, preferably of cell wall components, more preferably lipopolysaccharide, of microorganisms by administering an effective amount of a peptide or polypeptide or a pharmaceutical composition according to the present invention.

The peptides and polypeptides according to the present invention exhibit endotoxin-neutralizing activity. Therefore these substances may be employed to bind bacterial components, in particular cell wall components, and consequently to neutralize its biological activity.

Yet another aspect of the present invention relates to a method of neutralizing the biological activity of bacterial components, preferably of cell wall components, more preferably lipopolysaccharide, of microorganisms or treating a mammal, in particular a human individual, suffering from a microbial infection or septic shock by administering an effective amount of a peptide or polypeptide or a pharmaceutical composition according to the present invention.

The therapeutically and prophylactically effective amount is preferably from about 0.5 mg/kg to about 100 mg/kg body weight, more preferably from about 1 mg/kg to about 20 mg/kg, and most preferably from about 2 mg/kg to about 10 mg/kg. For dermal application, the compounds can be administered at a concentration high enough to rapidly kill the target organism (at least 10-100 times the MIC or 100-1000 µg/ml). For intraperitoneal application, the therapeutic range is preferably from about 7.5 mg/kg to about 75 mg/kg. In case of co-application with conventional antibiotics, the therapeutically effective amount is reduced by a factor of 10 to 100.

Another aspect of the present invention relates to a method for manufacturing a peptide according to the present invention having an N-terminal proline residue comprising the steps:

providing a host cell comprising a nucleic acid molecule encoding a fusion polypeptide or protein comprising a peptide according to the present invention having an N-terminal proline residue, wherein the peptide is fused C-terminally to said polypeptide or protein having a C-terminal aspartate, expressing and isolating said fusion polypeptide or protein, subjecting the isolated fusion polypeptide or protein to a pH value between 0.5 and 4 (Skribanek Z. et al., *J. Pept. Sci.* 8: 398-406 (2002)).

In the course of the reduction of the pH value the polypeptide or protein is preferentially incubated at 85° C. for one hour in, e.g., 90 mM HCl. The resulting peptides are preferably purified by reversed phase high performance liquid chromatography (RP-HPLC) and optionally identified and characterized by mass spectral analysis.

Another aspect of the present invention relates to a method of adsorption and removal or inactivation of bacteria or bacterial components from samples comprising the steps of contacting said sample with immobilized peptide according to the present invention.

The antimicrobial and endotoxin-neutralizing/-binding agent of the present invention can be applied to a surface of a suitable material or mixed with a suitable material to produce an antimicrobial material. Such an antimicrobial material can be used in the various forms of a bead, a film, a plate, a monofilament, an unwoven fabric, sponge, cloth, a knitted fabric, a short fiber, a tube, a hollow fiber, or the like. More particularly, it can be used for an artificial organ, a catheter, a suture (joining fiber) for surgical operation, a dialysis membrane, and the like as well as sanitary goods, an antimicrobial filter, and the like.

The device or implant may be used as endotoxin-removing agent comprising the peptide of the present invention immobilized to an insoluble carrier. The endotoxin-removing agent of the present invention is based on application of a high endotoxin bindability of the peptide of the present invention to adsorption and removal of endotoxin.

The shape of the insoluble carrier to which the peptide of the present invention is immobilized is not limited particularly and there can be cited various forms, for example, forms of membrane (filter type, hollow type, tube type, flat membrane type, etc.), granule, latex, chip, powder, and microplate.

The material of the insoluble carrier is not limited particularly either and there can be cited various materials, for example, polystyrene materials, polypropylene materials, polyamide materials, cellulose materials, agarose materials, polyacrylamide materials, dextran materials and vinyl polymer materials.

The method for immobilizing the peptide of the present invention to the insoluble carrier is not limited particularly either and the immobilization of the peptide of the present invention can be achieved by utilizing general methods used as a preparation method for immobilized enzymes such as a physical adsorption method, an ionic bond method, a covalent bond method, an inclusion method.

For example, for the insoluble carriers made of polystyrene materials or polypropylene materials, the peptide of the present invention can be physically immobilized. Also, for example, the insoluble carriers made of polyamide materials, cellulose materials, agarose materials, polyacrylamide materials, dextran materials, or vinyl polymer materials, the peptide of the present invention can be chemically immobilized. As the chemical immobilizing (binding) method, there can be cited, for example, a diazotization method in which diazo coupling is carried out utilizing an aromatic amino group in the insoluble carrier, a CNBr method in which a peptide bond is formed by activating a hydroxyl group in the insoluble carrier with CNBr, an acid azide method in which a peptide bond is formed by using a hydrazine derivative of the insoluble carrier, an alkylation method in which a peptide is alkylated utilizing a reactive functional group such as a halogen in the insoluble carrier, a cross linking method in which a crosslinking agent reactive with a free amino group such as glutaraldehyde crosslinks between the insoluble carrier and the free amino group in the peptide, a carbodiimide method, an epoxy activation method, and methods in which a bond is formed through a spacer using one of the above-described methods. An appropriate method can be selected from these known methods depending on the kind of the insoluble carrier for application in bonding of peptide of the present invention.

The insoluble carrier to which the peptide of the present invention is immobilized is brought into contact with a solution in which removal of endotoxin is desired to form a complex of the endotoxin in the solution and the insoluble carrier to which the peptide of the present invention is immobilized, and then the complex thus formed is removed, whereby the endotoxin in the solution can be removed.

The method for contacting the insoluble carrier to which the peptide of the present invention is immobilized with the solution in which removal of endotoxin is desired is not limited particularly and known solid-liquid contacting means can be used. For example, a method in which a solution is passed through a filter-shaped or hollow fiber-shaped insoluble carrier or over a flat membrane-shaped insoluble carrier, a method in which a solution is passed through a column charged with a granular insoluble carrier, a method in which a solution is charged in a microplate-shaped well and the solution is left to stand for a certain time and then the solution is separated, a method in which a solution is added onto an insoluble carrier of any shape and shaken or left to stand for a certain time and then usual solid-liquid separation means (filtration, centrifugation, aspiration, decantation, etc.) can be used to obtain a solution which is free of endotoxin, or the like.

The solution in which removal of endotoxin is desired is not limited particularly and examples thereof include solutions used in a pharmaceutical production plant, a medical installation, and the like, more particularly, dialysate fluid, parenteral fluid, blood, pharmaceuticals, superpure water, and the like but not limited thereto.

One aspect of the invention is an antimicrobial compound, i.e., that inhibit, prevent, or destroy the growth or proliferation of microbes such as bacteria, fungi, or the like. These compounds are peptides or lipopeptides of the general formula as outlined herein.

Another aspect of the invention is a method of treating endotoxaemia by neutralizing the biological activity of bacterial components, preferably from cell walls such as endotoxin by applying peptides or lipopeptides of the general formula as outlined herein.

The following examples and figures are provided as guidance for those of ordinary skill in the art, and are not intended to limit the scope of the claimed invention in any way.

EXAMPLES

Example 1

Peptide and Lipopeptide Synthesis

Figure 1:
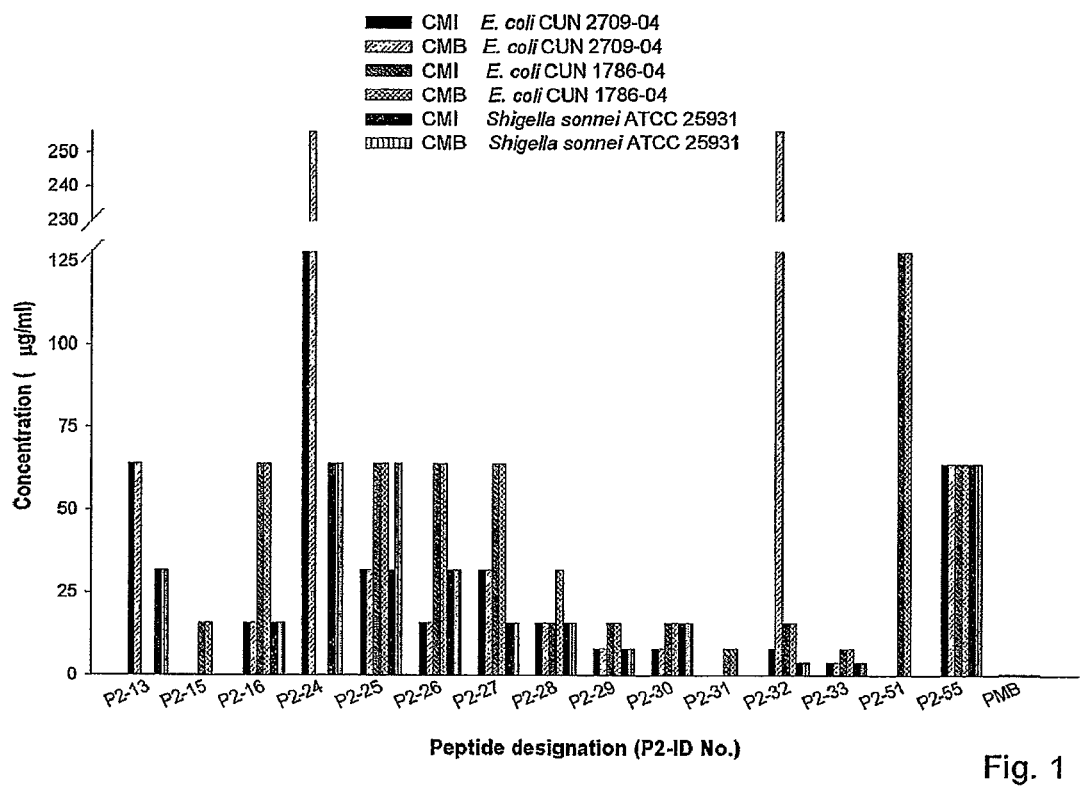
FIG. 1 shows the minimal inhibitory concentration (MIC) and minimal bactericidal concentration (MBC) of selected peptides (see peptide designation) and polymyxin (PMB) for two E. coli strains and Shigella sonnei as indicated in the figure.

The peptides were synthesized by simultaneous multiple peptide synthesis following standard Fmoc synthetic protocols (Houghten, *Proc. Natl. Acad. Sci. USA* 82:5131-5135 (1985)). The resin for each peptide is compartmentalized in a polypropylene mesh packet, which allowed to carry out all common synthetic steps in a common reaction vessel (i.e., washes, deprotection and neutralization steps), while the desired coupling steps were performed by treating each packet with separate appropriate amino acid solutions. The lipophilic acid was bound to the N-terminus in a similar strategy as that used when coupling a protected amino acid. The side chains of lysine and tryptophan were protected with a tBoc group, arginine with pentamethylbenzofuran-5-sulfonyl group, cysteine, glutamine and asparagine with trityl, aspartic acid, glutamic acid, tyrosine, serine and threonine with tbutyl. Final cleavage was performed by treatment with trifluoroacetic acid (Fields et al., *Int. J. Peptide Prot. Res.* 35:161-214 (1990)). The identity and purity of the peptides were determined by mass spectral analysis interfaced with a liquid chromatography system (Finnigan LCQ) and analytical reversed phase high performance liquid chromatography (RP-HPLC) using a Beckman System Gold HPLC. The peptides and lipopeptides were purified by preparative RP-HPLC using a Waters Milliprep 300 preparative HPLC with a Foxy fraction collector. Acetic acid (up to 95%) or acetonitrile (up to 50%) solution was used to solubilize the lipopeptides for purification.

Example 2

Antimicrobial Assays

Each peptide and lipopeptide was tested for minimum inhibitory concentration (MIC) against a list of bacteria:
Escherichia coli ATCC 25922, Escherichia coli DC2, Klebsiella oxytoca ATCC 8724, Acinetobacter baumanii CUN 10817-01, Pseudomonas aeruginosa: CUN 4158-02, Stenotrophomonas maltophilia: CUN 3998-00, Brucella abortus 9.49 per-, *Yersinia pestis* KIM pYV-, *Escherichia coli* CUN 2709-04, *Escherichia coli* CUN 1786-04, *Shigella sonnei* ATCC 25931, *Salmonella minnesota* HL63 (S), *Salmonella Minnesota* R60 HL100 (Ra), *Salmonella minnesota* R7 HL44 (Rd1), *Salmonella Minnesota* R595 HL111 (Re) *Bordetella bronquiseptica*: CUN 11844-99, *Bordetella bronquiseptica* RB50, *Haemophilus influenzae* CUN 6277-04, *Neisseria meningitidis* CUN 6395-04, *Enterococcus faecalis* ATCC 29212, *Staphylococcus aureus* ATCC 25923, *Streptococcus agalactiae* CUN 4783-03, *Enterococcus faecalis* ATCC 51299, *Staphylococcus* aureus CUN 3792-99, *Staphylococcus epidermidis* ATCC 12228, *Staphylococcus epidermidis* CUN 5-93, *Streptococcus pneumoniae* ATCC 49619

Freshly grown bacterial cultures were inoculated and diluted in Mueller Hinton (MH) broth for an approximate final assay concentration of $1-5 \times 10^5$ CFU/ml. A viable count of the bacterial suspension was determined by diluting the culture with MH broth and plating 100 µl of appropriate 10-fold dilution onto a MH agar plate. The MIC following overnight incubation at 37° C. was determined in 96 well tissue culture plates by a broth microdilution method according to guidelines of the National Committee for Clinical Laboratory Standard. Thus, 100 µl bacterial suspension was mixed with 100 µl peptide or lipopeptide solution in MH broth in 96-well flat bottom plates and incubated overnight at 37° C. The absorbance at 620 nm of each well was measured prior and following the incubation. All peptide and lipopeptides were tested at serial two-fold dilutions starting at 250 µg/ml in duplicate. Activity of peptides was compared to cells in MH broth (0% inhibition) and MH broth alone (100% inhibition). The MIC was defined as the lowest concentration of peptide or lipopeptide at which there was no change in OD between time 0 and overnight incubation. Commercially available antibiotics were used as standard controls in every assay.

Minimum bactericidal concentration (MBC) was defined as the lowest concentration of the antimicrobial that killed 99.9% of starting inocula and was determined as recommended by CLSI/NCCLS. Briefly, 100 µl of suspension was taken from those wells where growth was undetectable and plated onto MH plates. Plates were incubated at 37° C. for 24 h (FIG. 1).

Example 3

Synergistic Activity with Conventional Antibiotics

The outer membrane of Gram negative bacteria acts as a permeability barrier against hydrophobic compounds. To measure the permeabilizing activity of peptides, two methods were used. Both assays have the same basis: a membrane permeabilized by peptides allows hydrophobic substances (NPN) to access the lipid bilayer, and for novobiocin to reach its inner target (DNA gyrase). Those tests were performed on *P. aeruginosa* 4158-02 (CUN), due to lower permeability, intrinsic in this bacteria.

Figure 2:
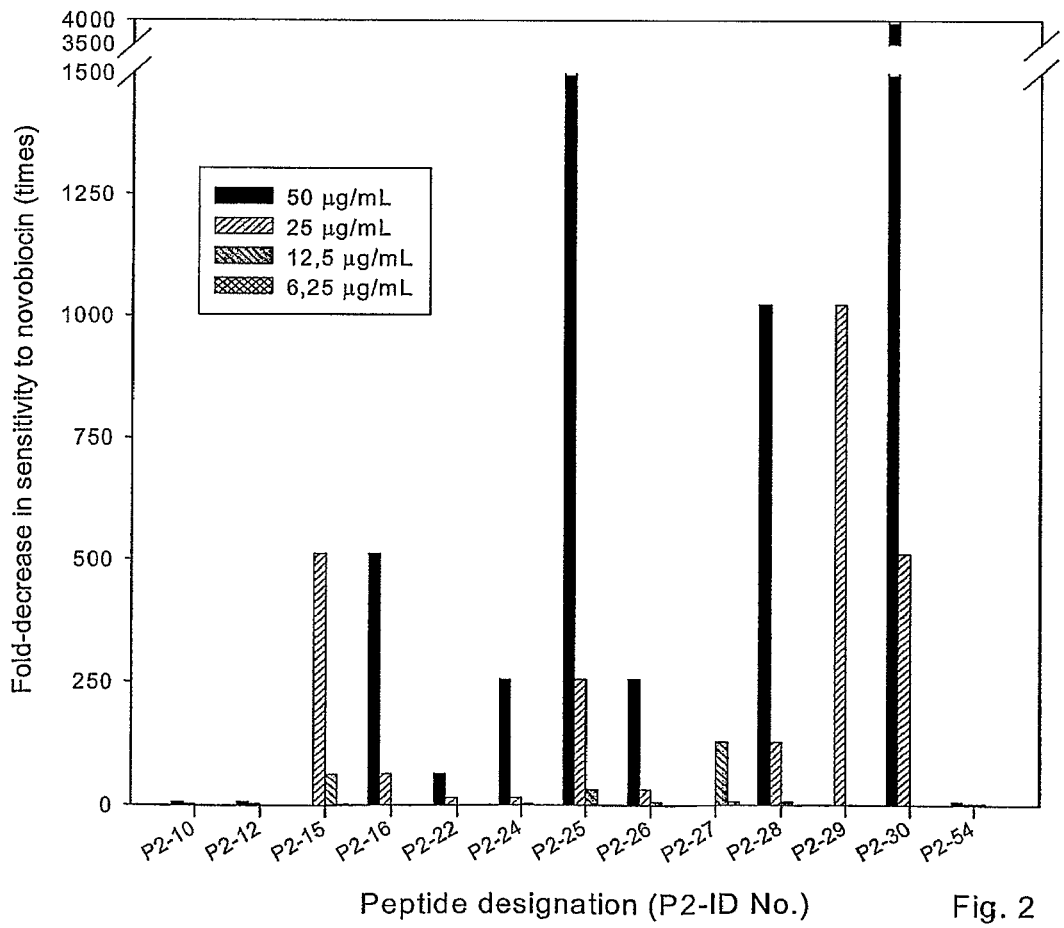
FIG. 2 shows the decrease of minimal inhibitory concentration of novobiocin upon addition of defined amounts of selected peptide.

Novobiocin-Peptide Synergy Assay:

The permeabilizing activity of the peptides was measured by comparing the MIC of each peptide-novobiocin combination with that of the novobiocin alone according to a checkerboard titration method already published (Lorian V. Antimicrobials in laboratory Medicine", 1996 4th ed. pp. 330-396, Williams and Wilkins, Baltimore, Md.). To compare the permeabilizing activities of the peptides two indexes were determined: (i), The fractional inhibitory concentration (FIC) index was calculated according to the following equation: FIC index=(MIC of novobiocin tested combination)/(MIC of novobiocin alone)+(MIC of peptide in combination)/(MIC of peptide alone). The interaction was defined as synergistic if the FIC index was $\leq 0.5$; (b), the MIC-Drop was defined as the ratio of novobiocin MICs in the absence and in the presence of a given peptide. One combination was considered as synergistic when its MIC-Drop was $\geq 4$ (FIG. 2).

Figure 3:
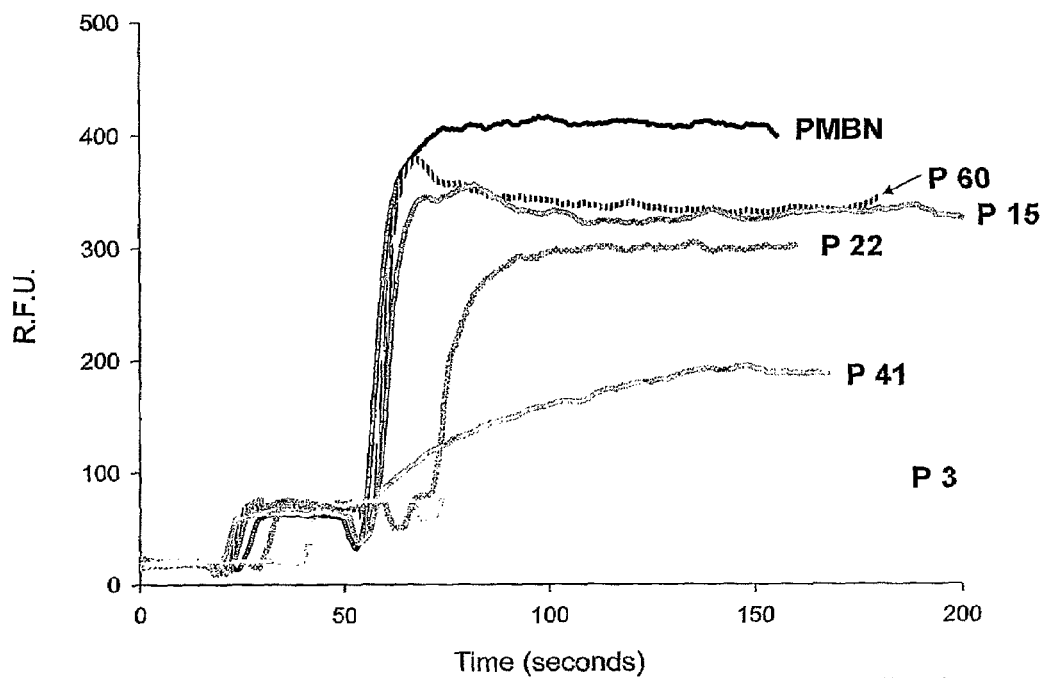
FIG. 3 shows the permeabilizing effect of selected peptides polymyxin B nonapeptide (PMBN) and a non-permeabilising peptide (P3) measured by fluorescence intensity increase due to partition of N-phenylnaphthylamine (NPN) into the cell envelope of E. coli. The sequence of the substances listed in the legend on the right side of the graph corresponds to the sequence of the curves in the graphs at their end-point.

Fluorometric Assay:

The fluorescence experiments were done as described by Loh and collaborators (1984. Antimicrob. Agents Chemother. 26:546-551) with some modifications. Briefly, bacteria were grown in LB broth to logarithmic phase, washed in 5 mM HEPES buffer (pH 7.2) and resuspended in the same buffer with 0.1% of glucose to a final absorbance of 0.5 at $\lambda=600$ nm. The fluorescence was measured at 37° C. in a fluorometer (LS-50, Perkin-Elmer) using an excitation wavelength of 350 nm and an emission wavelength of 420 nm. NPN was added to the suspension at a final concentration of 10 µM and, subsequently, peptides were added at a final concentration of 50 µg/ml (FIG. 3).

Example 4

Neutralization of TNF-α Secretion of Monocytes Stimulated by LPS

Figure 4:
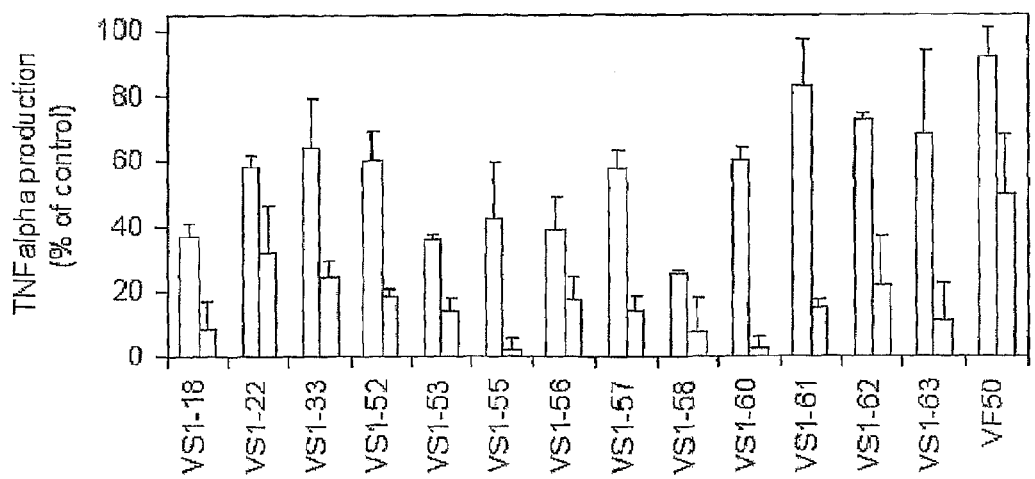
FIG. 4 shows the neutralization of TNF-α secretion of monocytes stimulated by LPS in the presence of selected peptides.

Inhibition of LPS-induced activation of human mononuclear cells by lactoferricin-derived peptides was measured using LPS Ra from the rough mutant strain R60 of *Salmonella enterica* (*Serovar minnesota*). The lipopolysaccharide was incubated with peptides (open bars, 0.1 µg/ml; filled bars, 1 µg/ml) for 30 min at 37° C. and added to the freshly isolated cells from healthy donors (final concentration: 1 ng/ml LPS). The amount of TNFα in the cell culture supernatant induced by LPS alone is used as untreated control (FIG. 4).

Example 5

Neutralization of Stimulation of Immune Cells of Killed Bacteria

Figure 5:
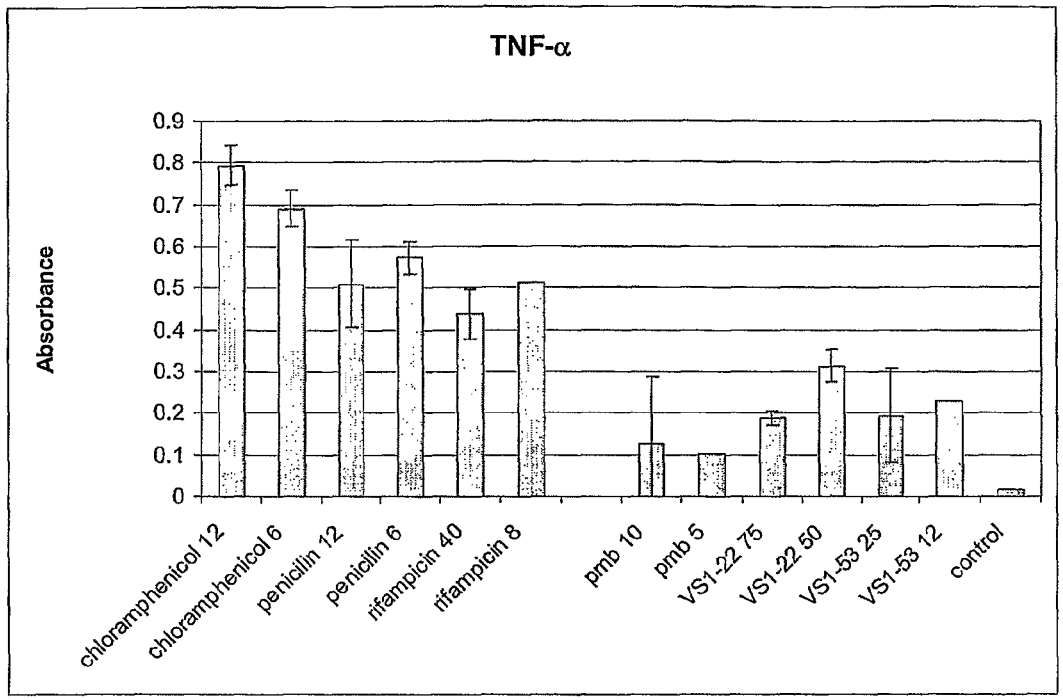
FIG. 5 shows the release of TNF-α in the presence of different antibiotics, polymyxin B (PMB) and selected peptides (see peptide designation).

Bacteria can be killed by different antibiotics, targeting different molecules essential for bacterial survival. When Gram-negative bacteria are killed, released LPS can stimulate production of cytokines, such as TNFα, or other inflammatory mediators. Comparison of well-established antimicrobial agents acting through different cellular targets with compounds of this invention were done in the following manner: bacteria (*E. coli* strain 0:111) were grown in LB medium to the absorbance at 600 nm of 0.4 and diluted 2500 fold in RPMI medium with added glucose. Different concentrations of antibiotics or peptides from this invention were added and incubated over night. 80 µl of cell suspension was added to the 100 µl containing $10^5$ MonoMac6 cells and after 15 hours the release of TNFα to the medium was determined using ELISA test. Results clearly show that chloramphenicol, penicilin and rifampicin, which killed bacterial cells, resulted in high stimulation of the monocytes, while the peptides VS1-22 and VS1-53 significantly inhibited the release of TNFα, similar as the toxic lipopeptide polymyxin B (FIG. 5).

Example 6

In Vivo Assays

Mouse Model of Acute Endotoxemia to Determine the Antiendotoxic Activity of the Peptides Mice are remarkably resistant to LPS-mediated septic shock. However, the sensitivity of mice to endotoxin can be potentiated by coinjecting LPS with galactosamine. Groups of 16-18 female ICR-CD1 mice of 20-25 g of weight were intraperitoneally injected with 200 µl of pyrogen-free saline containing a mixture of 0.3 µg of *E. coli* LPS and 18 mg of galactosamine. Previous experiments allowed to determine that such a combination was lethal for 90% ($LD_{90}$) of the animals 48 h after the injection. Immediately after this challenge, mice received a second intraperitoneal injection at a different site of the abdomen containing 150 µg of the peptide dissolved in 150 µl of 10% DMF pyrogen-free saline. In all the experiments a group of mice was left untreated whereas another group received 150 µg of polymyxin B. Mortality of the animals was monitored at daily intervals until 168 hours postchallenge. Under our experimental conditions, polymyxin B did not confer significant protection against endotoxic shock.

Rabbit Model to Determine the Antiendotoxic Activity of the Peptides:

The principle of lipid A-induced pro-inflammatory cytokine activity leading to hemorrhagic dermonecrosis (classical Shwartzmann reaction) was tested in rabbit, an animal model very close to humans in terms of sensitivity to LPS activity, and was compared to the inhibition of the lipid A-induced LAL enzymatic cascade activation leading to clot. Thereby, New Zealand White rabbits were injected in the shaved dorsal region with *S. minnesota* Re595 lipid A alone or with peptide 1:100 (w/w) (5 µg in 0.2 ml saline buffer; route i.d.). After 72-96 hours from injection, the derma of the animals were observed for the presence of open necrosis or the inhibition of it. Polymyxin B (PmB) was used as a control.

TABLE 4

Peptides from different claims showing positive correlation between "in vitro" vs "in vivo" test-analysis

| SEQ ID NO. (Modification) | Peptide Design. | Endpoint LAL activity[1] peptide: LPS Re595 100:1 (w/w) | Local Shwartzmann[2] reaction in rabbit peptide: LPS Re595 100:1 (w/w) |
|---|---|---|---|
| 25 | VS1-18 | NEGATIVE | NEGATIVE |
| 17 | VS1-15 | NEGATIVE | NEGATIVE |
| 17 (2,2-DMB[3]) | VS1-42 | NEGATIVE | NEGATIVE |
| 51 | VS1-22 | NEGATIVE | NEGATIVE |
| 51 (2,2-DMB) | VS1-52 | NEGATIVE | NEGATIVE |
| 75 (cyclo) | VF-50 | NEGATIVE | NEGATIVE |
| 77 | P2-11 | NEGATIVE | NEGATIVE |
| 78 | P2-19 | NEGATIVE | NEGATIVE |
| 79 | P2-18 | NEGATIVE | NEGATIVE |
| 12 | P1-12 | NEGATIVE | NEGATIVE |
| 20 | P1-39 | NEGATIVE | NEGATIVE |
| 69 | P1-63 | NEGATIVE | NEGATIVE |
| — | PmB | NEGATIVE | NEGATIVE |

[1]Limulus test(gel-clotting) sensibility 0.125 EU/ml corresponding to 10 pg/ml of LPS S. Minnesota Re595; results obtained with a minimum of 6 tests performed in triplicate by LAL assay, using stock solutions prepared in different days.
[2]Results obtained with a minimum of 3 dermal injections of the selected peptide in a minimum of 3 rabbits tested in different temporal experiments.
[3]2,2-DMB . . . 2,2-dimethylbutanoyl Example 7

Toxicity Tests Against Mammalian Cells

Figure 6:
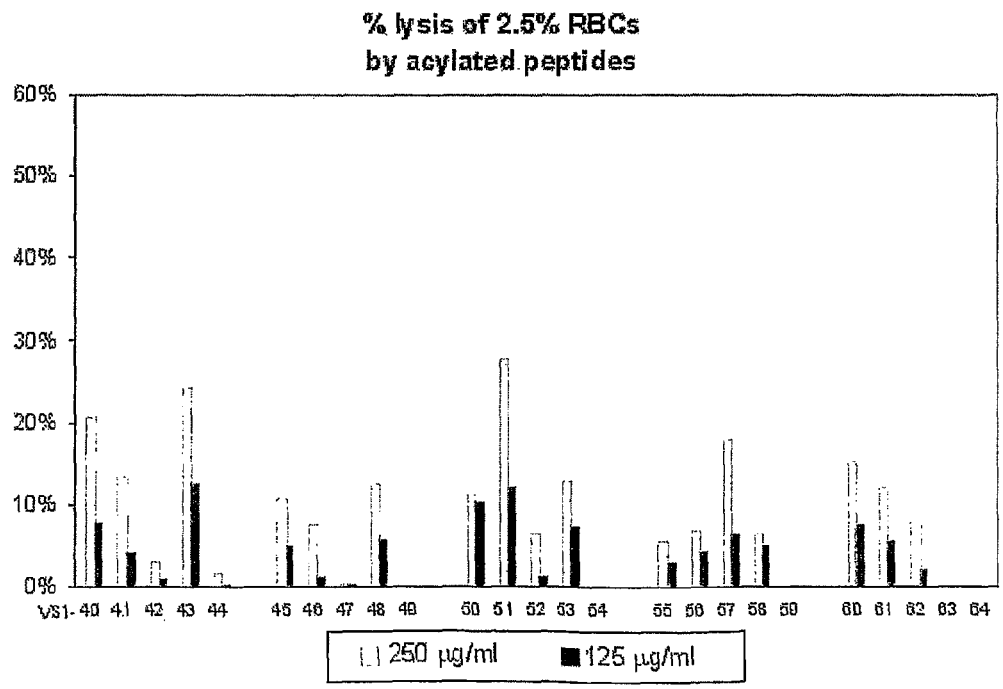
FIG. 6 shows the hemolytic activity of peptides containing N-acyl chains. Amount of peptides added to 2.5% human red blood cells is indicated in the figure.

The hemolytic activity of the peptides towards red blood cells, which were obtained from heparinized human blood, was determined by the release of haemoglobin following an hour incubation at 37°. Total release of haemoglobin (absorbance measured at 414 nm) was achieved by adding Triton X-100 (0.5% final concentration). Data for acylated peptides at concentrations above their MIC (5-50 fold depending on peptide and bacterial species) are shown (FIG. 6).

Furthermore, peptides displaying the highest membrane permeabilizing activity were selected and their toxicity towards human Hela cells was evaluated by the Trypan Blue dye exclusion test (Mishell, B. B., and S. M. Shiigi. 1980. Selected methods in cellular immunology. Freeman and Co., San Francisco. 14-17). When tested at 100 µg/ml all the peptides (n=16) showed no or negligible effects on the ability of the cells to exclude the dye.

Example 8

Purification of the Expressed Peptides

Figure 7:
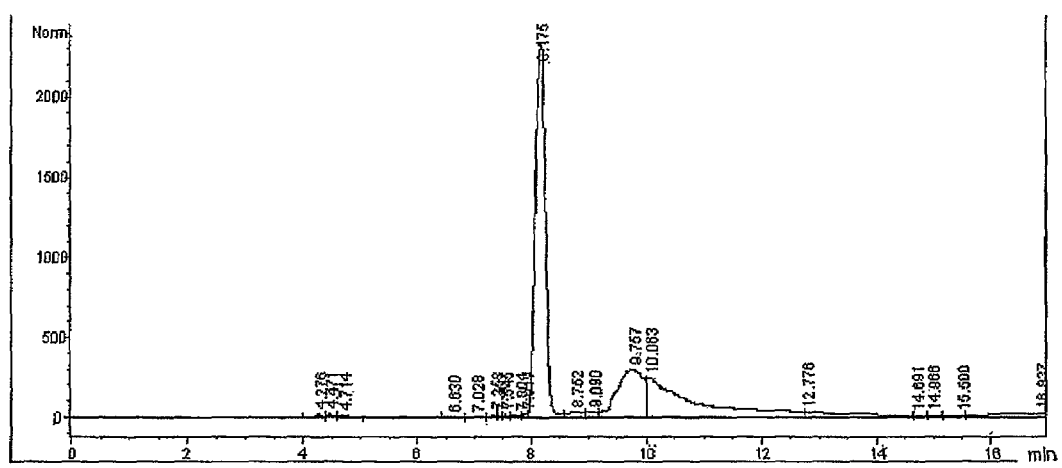
FIG. 7 shows the chromatogram of the HPLC separation of cleavage products of recombinant peptide. Fraction with retention time of 8.175 minutes contained the peptide.

To purify the recombinant proteins, the bacterial cell pellet from 1 liter was resuspended in 20 ml of lysis buffer (10 mM Tris pH=8.0, 1 mM EDTA, 0.1% DOC) and dispersed by sonication. The mixture was centrifuged at 12,000 rpm for 15 min at 4° C. to separate the soluble supernatant and the insoluble pellet fraction containing inclusion bodies. The insoluble inclusion body fraction containing KSI-P2-33 fusion protein was washed twice with 20 ml of washing buffer, containing 10 mM Tris pH=8.0, 1 mM EDTA and 0.1% DOC, twice with 10 mM Tris pH=8.0, 1 mM EDTA and 2 M urea and three times with 20 mM Tris pH=8.0. The insoluble inclusion bodies were dissolved in 10 ml of 6M guanidine-HCl, centrifuged and soluble supernatant dialyzed against 2 liters of deionized water which caused precipitation of KSI-P2-33. The fusion proteins (10 mg) were dissolved in 10 ml of 90 mM HCl, the mixtures were mixed 2 hours at 85° C. to cleave the aspartyl-prolyl bond between the fusion protein and peptides. Peptide released by acidic cleavage was purified by HPLC: reaction mixture was dried, dissolved in deionised water and injected onto the C5 RP-HPLC column (Sephasil) and eluted with a gradient from 5% acetonitrile, 5 mM HCl to 95% acetonitrile, 5 mM HCl. Peptide peak (FIG. 7) was detected by UV absorbance at 280 nm. The identity of peptide was determined by mass spectrometry.

Example 9

Antimicrobial Assays with Immobilized Peptides

Peptide P2-32 (500 µg) was covalently bound to the cyanuric chloride-activated magnetic particles (10 mg) (Chemicell, Product number 1314) using phosphate buffer saline pH=7.5. After mixing the suspension on a shaker for 2 hours at room temperature the blocking buffer (PBS pH=7.5 and 2% ethanolamine) were added and mixed the suspension on a shaker for 30 minutes at room temperatures. The particles were washed twice with PBS. Immobilized peptides were tested against *E. coli* (strain 0:111) grown in LB medium to the absorbance at 600 nm of 0.4 and diluted 2500 fold in LB medium. Different concentrations of magnetic particles immobilized with peptides were added and incubated over night. Results prevented bacterial growth at 50, 25 and 10 mg/ml concentrations of immobilized magnetic particles.

TABLE 5

| amount of added (mg) immobilized magnetic particles | vol (µl) of diluted E. coli in LB | bacterial growth |
|---|---|---|
| 5 | 100 | inhibited |
| 2.5 | 100 | inhibited |
| 1 | 100 | inhibited |
| 0.5 | 100 | not-inhibited |
| 0.25 | 100 | not-inhibited |

Example 10

Antifungal Activity

*C. neoformans* ATCC 32045 cultures were maintained on yeast medium (YM; Difco Laboratories, Detroit, Mich.) agar plates at 4° C. Prior to the assay, the cultures were grown on agar plates and incubated for 72 hrs at 26° C. Two colonies of these newly grown fungal cultures were then inoculated in 5 ml of 2×YM broth, vortexed, and diluted 10-fold in 2×YM broth, for an approximate final assay concentration of $1 \times 10^5$ to $5 \times 10^5$ CFU/ml. In 96-well tissue culture plates, fungal suspensions in 2×YM broth were added to the peptides dispensed at concentrations ranging from 1 mg/ml to 1 µg/ml derived from serial twofold dilutions in sterile water. The plates were then incubated for 72 hrs at 26° C. The relative percent growth of the fungi found for each test sample was determined by the optical density at 620 nm (OD620) by using a Titertek Multiskan Plus apparatus. The MIC was defined as the lowest concentration of the test sample that resulted in 2% growth, and the IC50 was defined as the test sample concentration that resulted in 50% growth inhibition. The IC50 were calculated by using a sigmoidal curve-fitting software program (Graphpad Prism; ISI Software, San Diego, Calif.). Results obtained for selected peptides are shown in Table 6.

| Peptide Designation | SEQ ID No. | C-terminal modification | average IC50 (µg/ml) | MIC (µg/ml) |
|---|---|---|---|---|
| VS1-13 | 4 | FWQRNIRIRR-NH2 | 8 | 32 |
| VS1-14 | 80(SEQ ID No. 4 retro) | RRIRINRQWF-NH2 | 12 | 32 |
| VS1-15 | 17 | FWQRNIRKWR-NH2 | 5 | 16 |
| VS1-16 | 66 | RWKRINRQWF-NH2 | 13 | 32 |
| VS1-17 | 24 | FWQRRIRKWR-NH2 | 5 | 32 |
| VS1-18 | 25 | FWQRRIRRWRR-NH2 | 7 | 32 |
| VS1-19 | 64 | PFWQRNIRKWR-NH2 | 3 | 8 |
| VS1-20 | 47 | FWRNIRKWR-NH2 | 4 | 16 |
| VS1-21 | 37 | FWRIRKWR-NH2 | 4 | 16 |
| VS1-22 | 51 | PFWRIRIRR-NH2 | 2 | 8 |
| VS1-23 | 59 | PFWRIRIRRD-NH2 | 4 | 8 |
| VS1-24 | 60 | PFFWRIRIRR-NH2 | 3 | 8 |
| VS1-25 | 52 | PFWRQRIRR-NH2 | 6 | 32 |
| VS1-26 | 81 | PFWRRQIRR-NH2 | 6 | 32 |
| VS1-27 | 53 | PFWRARIRR-NH2 | 8 | 32 |
| VS1-28 | 54 | PFWRKRIRR-NH2 | 8 | 32 |
| VS1-29 | 55 | PFWRKRLRR-NH2 | 9 | 32 |
| VS1-30 | 82 | PFWRKKLKR-NH2 | 10 | 32 |
| VS1-31 | 56 | PFWRKRWRR-NH2 | 8 | 32 |
| VS1-32 | 57 | PFWRRRIRR-NH2 | 9 | 32 |
| VS1-33 | 58 | PFWRRRWRR-NH2 | 9 | 32 |
| VS1-34 | 61 | PWRIRIRR-NH2 | 2 | 8 |
| VS1-35 | 83 | PWRRIRR-NH2 | 12 | 32 |
| VS1-36 | 84 | PWRRKIRR-NH2 | 11 | 62 |
| VS1-37 | 85 | PFWRRRIRIRR-NH2 | 9 | 32 |

-continued

| Peptide Designation | SEQ ID No. | C-terminal modification | | average IC50 (µg/ml) | MIC (µg/ml) |
|---|---|---|---|---|---|
| VS1-39 | 86 | | RRWFWRR-OH | 6 | 32 |
| VS1-40 | 17 | octanoyl | FWQRNIRKWR-NH2 | 2 | 8 |
| VS1-41 | 17 | 2-ethylhexanoyl | FWQRNIRKWR-NH2 | 4 | 8 |
| VS1-42 | 17 | 2,2-dimethyl-butanoyl | FWQRNIRKWR-NH2 | 6 | 16 |
| VS1-43 | 17 | 6-methyloctanoyl | FWQRNIRKWR-NH2 | 6 | 16 |
| VS1-44 | 17 | dicyclo-hexylacetyl | FWQRNIRKWR-NH2 | 4 | 16 |
| VS1-45 | 66 | octanoyl | RWKRINRQWF-NH2 | 2 | 4 |
| VS1-46 | 66 | 2-ethylhexanoyl | RWKRINRQWF-NH2 | 4 | 8 |
| VS1-47 | 66 | 2,2-dimethylbutanoyl | RWKRINRQWF-NH2 | 8 | 16 |
| VS1-48 | 66 | 6-methyloctanoyl | RWKRINRQWF-NH2 | 2 | 8 |
| VS1-50 | 51 | octanoyl | PFWRIRIRR-NH2 | 6 | 16 |
| VS1-51 | 51 | 2-ethylhexanoyl | PFWRIRIRR-NH2 | 3 | 8 |
| VS1-52 | 51 | 2,2-dimethylbutanoyl | PFWRIRIRR-NH2 | 2 | 4 |
| VS1-53 | 51 | 6-methyloctanoyl | PFWRIRIRR-NH2 | 6 | 16 |
| VS1-55 | 75 | octanoyl | FWRIRIRR-NH2 | 4 | 16 |
| VS1-56 | 75 | 2-ethylhexanoyl | FWRIRIRR-NH2 | 3 | 16 |
| VS1-57 | 75 | 2,2-dimethylbutanoyl | FWRIRIRR-NH2 | 2 | 4 |
| VS1-58 | 75 | 6-methyloctanoyl | FWRIRIRR-NH2 | 6 | 16 |
| VS1-60 | 43 | octanoyl | FWRRFWRR-NH2 | 10 | 32 |
| VS1-61 | 43 | 2-ethylhexanoyl | FWRRFWRR-NH2 | 6 | 16 |
| VS1-62 | 43 | 2,2-dimethyl-butanoyl | FWRRFWRR-NH2 | 4 | 16 |
| VS1-63 | 43 | 6-methyloctanoyl | FWRRFWRR-NH2 | 11 | 62 |
| VS1-49 | 66 | dicyclo-hexylacetyl | RWKRINRQWF-NH2 | 2 | 4 |
| VS1-54 | 51 | dicyolo-hexylacetyl | PFWRIRIRR-NH2 | 3 | 8 |
| VS1-59 | 75 | (dicyclo-)hexylacetyl | FWRIRIRR-NH2 | 14 | 62 |
| VS1-64 | 43 | (dicyclo-)hexylacetyl | FWRRFWRR-NH2 | 6 | 32 |
| VF50 | 75 | cyclo | FWRIRIFRR-NH2 | 2 | 8 |

The invention claimed is:

1. A peptide with antimicrobial or endotoxin-neutralizing activity, which has a length of up to 50 amino acid residues and which comprises an amino acid sequence selected from: FWQRIRKVR (SEQ ID NO: 1), FWQRRIRKVRR (SEQ ID NO: 2), FWQRNIRIRR (SEQ ID NO: 4), FWQRNIRVR (SEQ ID NO: 6), FWQRNIRKVRR (SEQ ID NO: 7), FWQRNIRKVKK (SEQ ID NO: 8), FWQRNIRKVRRR (SEQ ID NO: 9), FWQRNIRKVKKK (SEQ ID NO: 10), FWQRNIRKVRRRR (SEQ ID NO: 11), FWQRNIRKVRRRI (SEQ ID NO: 12), FWQRNIRKVKKKK (SEQ ID NO: 13), FWQRNIRKVKKKI (SEQ ID NO: 14), FWQRNIRKIR (SEQ ID NO: 15), FWQRNIRKLR (SEQ ID NO: 16), FWQRNIRKWR (SEQ ID NO: 17), FWQRNWRKVR (SEQ ID NO: 18), FWQRNFRKVR (SEQ ID NO: 19), FWQRNYRKVR (SEQ ID NO: 20), FWQRNIRKVS (SEQ ID NO: 21), FWQRRIRIRR (SEQ ID NO: 22), FWQRPIRKVR (SEQ ID NO: 23), FWQRRIRKWR (SEQ ID NO: 24), FWQRRIRRWRR (SEQ ID NO: 25), FWPRNIRKVR (SEQ ID NO: 26), FWARNIRKVR (SEQ ID NO: 27), FWIRNIRKVR (SEQ ID NO: 28), FWLRNIRKVR (SEQ ID NO: 29), FWVRNIRKVR (SEQ ID NO: 30), FWQRNIFKVR (SEQ ID NO: 31), FWQRNIYKVR (SEQ ID NO: 32), FWRIRKWR (SEQ ID NO: 37), FWRIRKVR (SEQ ID NO: 38), FWRRWIRR (SEQ ID NO: 41), FWRGWRIRR (SEQ ID NO: 42), FWRRFWRR (SEQ ID NO: 43), FWRWRWR (SEQ ID NO: 44), FWRIWRWR (SEQ ID NO: 45), FWRIWRIWR (SEQ ID NO: 46), FWRNIRKWR (SEQ ID NO: 47), FWRRRIRIRR (SEQ ID NO: 48), FIWRWRWR (SEQ ID NO: 49), PFWRWRIWR (SEQ ID NO: 50), PFWRIRIRR (SEQ ID NO: 51), PFWRQRIRR (SEQ ID NO: 52), PFWRARIRR (SEQ ID NO: 53), PFWRKRIRR (SEQ ID NO: 54), PFWRKRLRR (SEQ ID NO: 55), PFWRKRWRR (SEQ ID NO: 56), PFWRRRIRR (SEQ ID NO: 57), PFWRRRWRR (SEQ ID NO: 58), PFWRIRIRRD (SEQ ID NO: 59), PFFWRIRIRR (SEQ ID NO: 60), PWRIRIRR (SEQ ID NO: 61), RFWQRNIRKVRR (SEQ ID NO: 62), RFWQRNIRKYR (SEQ ID NO: 63), PFWQRNIRKWR (SEQ ID NO: 64), RFRWQRNIRKYR (SEQ ID NO: 65), RWKRINRQWF (SEQ ID NO: 66), KRFSFKKC (SEQ ID NO: 68), KRWSWKK (SEQ ID NO: 69), FRFSFKK (SEQ ID NO: 70), RRFWFRR (SEQ ID NO: 71), FWRNIRIRR (SEQ ID NO: 72), FWQRIRIRR (SEQ ID NO: 73), FWRWRIWR (SEQ ID NO: 74), FWRIRIRR (SEQ ID NO: 75), FWRNIRIWRR (SEQ ID NO: 76), FWRNIRIRR (SEQ ID NO: 77), RFWQRNIRIRR (SEQ ID NO: 78), RWQRNIRIRR (SEQ ID NO: 79), RRIRINRQWF (SEQ ID NO: 80), PFWRRQIRR (SEQ ID NO: 81), PFWRKKLKR (SEQ ID NO: 82), PWRRIRR (SEQ ID NO: 83), PWRRKIRR (SEQ ID NO: 84), and PFWRRIRIRR (SEQ ID NO: 85).

2. The peptide of claim 1 comprising an amino acid sequence selected from: FWQRIRKVR (SEQ ID NO: 1), FWQRRIRKVRR (SEQ ID NO: 2), FWQRNIRIRR (SEQ ID NO: 4), FWQRNIRVR (SEQ ID NO: 6), FWQRNIRKVRR (SEQ ID NO: 7), FWQRNIRKVKK (SEQ ID NO: 8), FWQRNIRKVRRR (SEQ ID NO: 9), FWQRNIRKVKKK (SEQ ID NO: 10), FWQRNIRKVRRRR (SEQ ID NO: 11), FWQRNIRKVRRRI (SEQ ID NO: 12), FWQRNIRKVKKKK (SEQ ID NO: 13), FWQRNIRKVKKKI (SEQ ID NO: 14), FWQRNIRKIR (SEQ ID NO: 15), FWQRNIRKLR (SEQ ID NO: 16), FWQRNIRKWR (SEQ ID NO: 17), FWQRNWRKVR (SEQ ID NO: 18), FWQRNFRKVR (SEQ ID NO: 19), FWQRNYRKVR (SEQ ID NO: 20), FWQRNIRKVS (SEQ ID NO: 21), FWQRRIRIRR (SEQ ID NO: 22), FWQRPIRKVR (SEQ ID NO: 23), FWQRRIRKWR (SEQ ID NO: 24), FWQRRIRRWRR (SEQ ID NO: 25), FWPRNIRKVR (SEQ ID NO: 26), FWARNIRKVR (SEQ ID NO: 27), FWIRNIRKVR (SEQ ID NO: 28), FWLRNIRKVR (SEQ ID NO: 29), FWVRNIRKVR (SEQ ID NO: 30), FWQRNIFKVR (SEQ ID NO: 31), FWQRNIYKVR (SEQ ID NO: 32), FWRIRKWR (SEQ ID NO: 37), FWRIRKVR (SEQ ID NO: 38), FWRRWIRR (SEQ ID NO: 41), FWRGWRIRR (SEQ ID NO: 42), FWRRFWRR (SEQ ID NO: 43), FWRWRWR (SEQ ID NO: 44), FWRIWRWR (SEQ ID NO: 45), FWRIWRIWR (SEQ ID NO: 46), FWRNIRKWR (SEQ ID NO: 47), and FWRRRIRIRR (SEQ ID NO: 48).

3. The peptide of claim 1 comprising an amino acid sequence selected from: FWRIRKWR (SEQ ID NO: 37), FWRIRKVR (SEQ ID NO: 38), FWRRWIRR (SEQ ID NO: 41), FWRGWRIRR (SEQ ID NO: 42), FWRRFWRR (SEQ ID NO: 43), FWRWRWR (SEQ ID NO: 44), FWRIWRWR (SEQ ID NO: 45), FWRIWRIWR (SEQ ID NO: 46), FWRNIRKWR (SEQ ID NO: 47) and FWRRRIRIRR (SEQ ID NO: 48).

4. The peptide of claim 1 comprising an amino acid sequence selected from: PFWRWRIWR (SEQ ID NO: 50), PFWRIRIRR (SEQ ID NO: 51), PFWRQRIRR (SEQ ID NO: 52), PFWRARIRR (SEQ ID NO: 53), PFWRKRIRR (SEQ ID NO: 54), PFWRKRLRR (SEQ ID NO: 55), PFWRKRWRR (SEQ ID NO: 56), PFWRRRIRR (SEQ ID NO: 57), PFWRRRWRR (SEQ ID NO: 58), PFWRIRIRRD (SEQ ID NO: 59), PFFWRIRIRR (SEQ ID NO: 60), PWRIRIRR (SEQ ID NO: 61), PFWRRQIRR (SEQ ID NO: 81), PFWRKKLKR (SEQ ID NO: 82), PWRRIRR (SEQ ID NO: 83), PWRRKIRR (SEQ ID NO: 84) and PFWRRIRIRR (SEQ ID NO: 85).

5. The peptide of claim 1 comprising an amino acid sequence selected from: FWRNIRIRR (SEQ ID NO: 72), FWQRIRIRR (SEQ ID NO: 73), FWRWRIWR (SEQ ID NO: 74), FWRIRIRR (SEQ ID NO: 75), FWRNIRIWRR (SEQ ID NO: 76) and FWRNIRIRR (SEQ ID NO: 77).

6. The peptide of claim 1 comprising an amino acid sequence selected from: RFWQRNIRKVRR (SEQ ID NO: 62), RFWQRNIRKYR (SEQ ID NO: 63), PFWQRNIRKWR (SEQ ID NO: 64), RFRWQRNIRKYRR (SEQ ID NO: 65), RWKRINRQWF (SEQ ID NO: 66), KRFSFKKC (SEQ ID NO: 68), KRWSWKK (SEQ ID NO: 69), FRFSFKK (SEQ ID NO: 70), RRFWFRR (SEQ ID NO: 71), RFWQRNIRIRR (SEQ ID NO: 78), and RWQRNIRIRR (SEQ ID NO: 79).

7. The peptide of claim 1 comprising an amino acid sequence selected from: FIWRWRWR (SEQ ID NO: 49), and RRIRINRQWF (SEQ ID NO: 80).

8. The peptide of claim 1, wherein the C-terminus consists of a group further defined as a N-methylamido group, a carboxyl group, an amide group, an ester group, an ether group, or a ketone group.

9. The peptide of claim 8, wherein the group contains 1 to 120 carbon atoms.

10. The peptide of claim 9, wherein the group contains from 1 to 10 carbon atoms.

11. The peptide of claim 8, wherein the group is an N-methylamido group.

12. The peptide of claim 1, wherein an acyl group is bound to the N-terminus or C-terminus of the peptide.

13. The peptide of claim 12, wherein the acyl group is a hydrophobic chain further defined as a saturated or unsaturated linear or branched acyl chain of $C_2$-$C_{20}$, benzyl-derivatives, or F-moc.

14. The peptide of claim 12, wherein the acyl group is a Dodecanoyl-group, Decanoyl-group, Octanoyl-group, Hexanoyl-group, 2-Methylhexanoyl-group, 2-Ethylhexanoyl-group, 2-Propylpentanoyl-group, 2-Butyloctanoyl-group, 2,2-dimethylbutanoyl-group, 2-methylpentanoyl-group, 3-methylpentanoyl-group, 4-methylpentanoyl-group, 6-methyloctanoyl-group, Benzyl-group, or dicyclohexylacetyl-group.

15. A pharmaceutical composition comprising a peptide of claim 1.

16. The composition of claim 15, further comprising at least one further antimicrobial or anti-septic agent.

17. The composition of claim 15, further comprising a pharmaceutically acceptable excipient.

18. The peptide of claim 1, further defined as comprising the amino acid sequence FWQRNIRIRR (SEQ ID NO: 4).

19. The peptide of claim 1, further defined as comprising the amino acid sequence FWQRNIRKVRRRI (SEQ ID NO: 12).

20. The peptide of claim 1, further defined as comprising the amino acid sequence FWQRNIRKVKKKI (SEQ ID NO: 14).

21. The peptide of claim 1, further defined as comprising the amino acid sequence FWQRNIRKWR (SEQ ID NO: 17).

22. The peptide of claim 1, further defined as comprising the amino acid sequence FWQRRIRRWRR (SEQ ID NO: 25).

23. The peptide of claim 1, further defined as comprising the amino acid sequence FWRIRKWR (SEQ ID NO: 37).

24. The peptide of claim 1, further defined as comprising the amino acid sequence FWRRFWRR (SEQ ID NO: 43).

25. The peptide of claim 1, further defined as comprising the amino acid sequence FWRIWRWR (SEQ ID NO: 45).

26. The peptide of claim 1, further defined as comprising the amino acid sequence PFWRIRIRR (SEQ ID NO: 51).

27. The peptide of claim 1, further defined as comprising the amino acid sequence PFWRKRWRR (SEQ ID NO: 56).

28. The peptide of claim 1, further defined as comprising the amino acid sequence PFWRRRWRR (SEQ ID NO: 58).

29. The peptide of claim 1, further defined as comprising the amino acid sequence PFWRIRIRRD (SEQ ID NO: 59).

30. The peptide of claim 1, further defined as comprising the amino acid sequence PFFWRIRIRR (SEQ ID NO: 60).

31. The peptide of claim 1, further defined as comprising the amino acid sequence PWRIRIRR (SEQ ID NO: 61).

32. The peptide of claim 1, further defined as comprising the amino acid sequence FWRWRIWR (SEQ ID NO: 74).

33. The peptide of claim 1, further defined as comprising the amino acid sequence FWRIRIRR (SEQ ID NO: 75).

34. The peptide of claim 1, further defined as comprising the amino acid sequence PFWRRIRIRR (SEQ ID NO: 85).

* * * * *

UNITED STATES PATENT AND TRADEMARK OFFICE
CERTIFICATE OF CORRECTION

PATENT NO. : 7,960,339 B2  
APPLICATION NO. : 12/373272  
DATED : June 14, 2011  
INVENTOR(S) : Blondelle et al.

Page 1 of 1

It is certified that error appears in the above-identified patent and that said Letters Patent is hereby corrected as shown below:

Title Page Add

Item

-- (30) U.S. Application Priority Data

60/906,948    March 14, 2007 --

Signed and Sealed this
Twenty-seventh Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,960,339 B2 | Page 1 of 1 |
| APPLICATION NO. | : 12/373272 | |
| DATED | : June 14, 2011 | |
| INVENTOR(S) | : Sylvie E. Blondelle et al. | |

It is certified that error appears in the above-identified patent and that said Letters Patent is hereby corrected as shown below:

In Title Page, item (73) Assignee, delete "Österreichische Akademie der Wissenschaften, Graz (AT)" and insert --pba3 BioMed GmbH, Graz (AT)-- therefor.

Signed and Sealed this
Twentieth Day of December, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,960,339 B2 | Page 1 of 1 |
| APPLICATION NO. | : 12/373272 | |
| DATED | : June 14, 2011 | |
| INVENTOR(S) | : Sylvie E. Blondelle et al. | |

It is certified that error appears in the above-identified patent and that said Letters Patent is hereby corrected as shown below:

This certificate supersedes the Certificate of Correction issued September 27, 2011. The certificate should be vacated since there is no evidence of priority claimed for "60/906,648 March 14, 2007" in the patent. The U. S. Application Priority Data as printed on title page of patent is correct. No Certificate of Correction should have been issued for this patent number.

Signed and Sealed this
Third Day of January, 2012

David J. Kappos
*Director of the United States Patent and Trademark Office*